US007354710B2

(12) United States Patent
Hogan et al.

(10) Patent No.: US 7,354,710 B2
(45) Date of Patent: Apr. 8, 2008

(54) METHODS AND DEVICES BASED UPON A NOVEL FORM OF NUCLEIC ACID DUPLEX ON A SURFACE

(75) Inventors: Michael Hogan, Tucson, AZ (US); Sergy Lemeshko, Houston, TX (US); Yuri Belosludtsev, The Woodlands, TX (US); Tom Powdrill, College Station, TX (US); Rahul Mitra, Pearland, TX (US)

(73) Assignee: Genomics USA, Inc., Pearland, TX (US)

( * ) Notice: Subject to any disclaimer, the term of this patent is extended or adjusted under 35 U.S.C. 154(b) by 0 days.

(21) Appl. No.: 10/193,938

(22) Filed: Jul. 11, 2002

(65) Prior Publication Data

US 2003/0134299 A1 Jul. 17, 2003

Related U.S. Application Data

(60) Provisional application No. 60/304,500, filed on Jul. 11, 2001.

(51) Int. Cl.
*C12Q 1/68* (2006.01)
(52) U.S. Cl. ............................................. 435/6
(58) Field of Classification Search .................... 435/6; 536/24.3, 24.33
See application file for complete search history.

(56) References Cited

U.S. PATENT DOCUMENTS

| | | | | |
|---|---|---|---|---|
| 5,610,287 | A * | 3/1997 | Nikiforov et al. | 536/24.3 |
| 5,744,305 | A | 4/1998 | Fodor et al. | |
| 5,807,522 | A | 9/1998 | Brown et al. | |
| 5,959,098 | A | 9/1999 | Goldberg et al. | |
| 6,024,925 | A | 2/2000 | Little et al. | |
| 6,034,775 | A | 3/2000 | McFarlend et al. | |
| 6,048,695 | A | 4/2000 | Bradley et al. | |
| 6,077,674 | A | 6/2000 | Schleifer et al. | |
| 6,221,653 | B1 | 4/2001 | Caren et al. | |
| 6,271,957 | B1 | 8/2001 | Quate et al. | |
| 6,291,166 | B1 | 9/2001 | Gerdes et al. | |
| 6,316,608 | B1 * | 11/2001 | Reynolds et al. | 536/22.1 |
| 6,346,413 | B1 | 2/2002 | Fodor et al. | |
| 6,355,420 | B1 | 3/2002 | Chan | |
| 6,465,178 | B2 | 10/2002 | Chappa et al. | |
| 6,492,118 | B1 * | 12/2002 | Abrams et al. | 435/6 |
| 6,670,461 | B1 * | 12/2003 | Wengel et al. | 536/23.1 |
| 6,861,214 | B1 * | 3/2005 | Rampal et al. | 435/6 |

FOREIGN PATENT DOCUMENTS

WO 02/061146 8/2002

WO 03/006675 1/2003

OTHER PUBLICATIONS

Lvov et al., "Assembly of Thin Films by Means of Successive Deposition of Alternate Layers of DNA and Poly(allylamine)," *Macromolecules*, 1993, vol. 26, pp. 5396-5399.*
PCT Written Opinion for PCT/US02/22103, 6 pages, Mailed Jun. 10, 2003.
Belosludtsev Y et al., "DNA microarrays based on noncovalent oligonucleotide attachment and hybridization in two dimensions" *Anal. Biochem.* 292:250-256, 2001.
Belosludtsev Y et al., "Nearly instantaneous, cation-independent, high selectivity nucleic acid hybridization to DNA microarrays" *Biochem Biophys Res Commun.* 282:1263-1267, 2001.
Bensimon D et al., "Stretching DNA with a receding meniscus: Experiments and models" *Phys. Rev. Lett.* 74:4754-4757, 1995.
Cheung VG et al., "Making and reading microarrays" *Nature Genetics* 21(1 Suppl):15-19, 1999.
Dickerson RE, "DNA structure from A to Z" *Methods Enzymol.* 211:67-111, 1992.
Duggan DJ et al., "Expression profiling using cDNA microarrays" *Nature Genetics* 21(1 Suppl):10-14, 1999.
Gao Q et al., "Drug-Induced DNA Repair: X-ray Structure of a DNA-Ditercalinium Complex" *Proc. Natl. Acad. Sci. USA* 88:2422-2426, Mar. 1991.
Holmstrom K et al., 1993, "A highly sensitive and fast nonradioactive method for detection of polymerase chain reaction products" *Anal. Biochem.* 209(2):278-283.
Koltover, I et al., "An inverted hexagonal phase of cationic liposome-DNA complexes related to DNA release and delivery" *Science*, www.sciencemag.org, vol. 281, pp. 78-81, Jul. 3, 1998.
Lebrun A et al., "Modelling extreme stretching of DNA" *Nucleic Acids Res.* 24:2260-2267, 1996.

(Continued)

*Primary Examiner*—Young J. Kim
(74) *Attorney, Agent, or Firm*—Benjamin Aaron Adler

(57) ABSTRACT

The present invention relates to simple method to fabricate DNA hybridization devices based upon adsorptive attachment of oligonucleotides to a positively charged surface. Such adsorbed oligonucleotide probes form a densely packed monolayer, which retains capacity for base-pair specific hybridization with a solution state nucleic acid target strand to form the duplex. However, both strand dissociation kinetics and the rate of DNase digestion suggest on symmetry grounds that solution-state nucleic acid binds to such adsorbed oligonucleotides to form a highly asymmetric and unwound duplex, with structural details that are substantially different from that known for the Watson-Crick DNA duplex. This novel nucleic acid duplex form can serve as the basis for a new class of hybridization device and methods for their use. It is also disclosed that new methods of nucleic acid duplex detection can be developed which are based upon the interaction of enzymes and dye labels with the unique structural characteristics of the non-helical duplex described herein. Preferred implementations of the invention include DNA microarrays, bead-based nucleic acid analysis, microelectronic devices to detect nucleic acid hybridization and more traditional methods of laboratory analysis, including hybridization on membranous and other solid supports.

7 Claims, 10 Drawing Sheets

OTHER PUBLICATIONS

Leger JF et al., 1999, *Phys. Rev. Lett.* 83:1066-1069, 1999.

Lemeshko SV et al., "Oligonucleotides form a duplex with non-helical properties on a positively charged surface" *Nucleic Acids Research* 29(14):3051-3058, 2001.

Lindsay SM, The Scanning Probe Microscope in Biology, draft available at http://green.la.asu.edu/review/chap_7(3-5).htm, printed Feb. 7, 2005.

McConnell KJ et al., "DNA structure: what's in charge?" *J. Mol. Biol.* 304:803-820, 2000.

Mizutaini, Tadaharu, "Adsorption Chromatography of Nucleic Acids on Silicone-Coated Porous Glass", *J. Biochem*, vol. 94, pp. 163-169, 1983.

RNeasy Micro Handbook, "For isolation of total RNA from microdissected tissues, small amounts of tissues, small amounts of fibrous tissues, small numbers of cells, and for RNA cleanup and concentration", Apr. 2003.

Rhodes D et al., "Helical periodicity of DNA determined by enzyme digestion" *Nature* 286:573-578, 1980.

Salditt, T. et al., "Self-assembled DNA-Cationic-Lipid complexes: Two-dimensional smectic ordering, correlations, and interactions" *The Amer Physical Society* vol. 58, No. 1, pp. 903, Jul. 1998.

Schena M et al., "Quantitative monitoring of gene expression patterns with a complementary DNA microarray" *Science* 270(5235):467-470, Oct. 20, 1995.

Singh, N. et al., "Boronate affinity adsorption of RNA: possible role of conformational changes" *Jrnl of Chromatography A*, 840, pp. 205-213, 1999.

Smith SB et al., "Overstretching B-DNA: the elastic response of individual double-stranded and single-stranded DNA molecules" *Science* 271:795-799, 1996.

Sowerby, S. et al., "Differential adsorption of nucleic acid bases: Relevance to the origin of life", PNAS, vol. 98, No. 3, pp. 820-822, Jan. 30, 2001.

Timofeev et al., "Binding Specificity and Stability of duplexes formed by modified oligonucleotides with a 4096-hexanucleotide mocroarray", *Nucleic Acids Research*, vol. 29, No. 12, pp. 2626-2634, 2001.

Wirth MJ, available at http://www.udel.edu/chem/wirth/oligos.html, printed Feb. 7, 2005.

A second set of Cy3-labeled DNA 50-mers were adsorbed on to a uniform cationic surface according to the solution dip method of Cel Associates (CSA-25; http://www.cel-1.com/).

* cited by examiner

A

B

DNase I digestion
of the targets a     b 12-wt-s-cy3    24-wt-s-cy3
hybridization    hybridization

1

2

3

4

5

6

METHODS AND DEVICES BASED UPON A NOVEL FORM OF NUCLEIC ACID DUPLEX ON A SURFACE

This application claims the benefit of U.S. Provisional Application Ser. No. 60/304,500 filed Jul. 11, 2001.

This work was supported, in part, by a grant from the National Cancer Institute grant number PO1CA75173. The government has certain rights in the invention.

BACKGROUND OF INVENTION

The double helix is known to form as a result of the hybridization of complementary nucleic acid strands in aqueous solution. In the helix, the negatively charged phosphate groups of each nucleic acid strand are distributed helically on the outside of the duplex and there, are available for interaction with cationic groups. Cation-coated solid supports are now widely used in biotechnology, especially for covalent attachment of cDNAs and oligonucleotides as surface-bound probes on microarrays. These cation surfaces can bind the nucleic acid backbone electrostatically through the phosphate moiety. Oligonucleotides of less than 100 nucleotides are better suited for hybridization on such supports than full length genes.

Microarray technology has revolutionized applied genomics (Cheung V G et al., 1999, *Nature Genetics* 21:15-19; Duggan D J et al., 1999, *Nature Genetics* 21:10-14). It is based upon hybridization of a surface-bound nucleic acid to a nucleic acid in solution to form a Watson-Crick double helix by a mixed phase reaction between complementary nucleic acid strands. The secondary structure of the resulting double helix is determined, in part, by base pairing and base stacking, in conjunction with the constraints imposed on phosphodiester backbone conformation and sugar pucker. Those interactions serve to define local base pairing and also the overall pitch of the helix. Although, in solution, the average pitch of the helix is near to 10 base pairs, structural studies have revealed a high degree of variability and flexibility of pitch angle, including the modeling-based prediction that a flat, non-helical ribbon-like structure might form under conditions of extreme mechanical distension (Leger J F et al., 1999, *Phys. Rev. Lett.* 83:1066-1069; Bensimon D et al., 1995, *Phys. Rev. Lett.* 74:4754-4757; Smith S B et al., 1996, *Science* 271:795-799; Lebrun A et al., 1996, *Nucl. Acids Res.* 24:2260-2267; and Marko J F, Feig M, and Pettitt B M *J. Phys. Chem.*, submitted (personal communication)) or upon the disruptive binding of an intercalator (Gao O et al., 1991, *Proc. Natl. Acad. Sci. USA* 88:2422-2426).

Nucleic acids may be covalently or noncovalently immobilized on a surface. Several means of covalent attachment of nucleic acids are known in the art. For example, oligonucleotides may be covalent coupling to a surface by chemical or photochemical crosslinking as commonly practiced following Northern and Southern blotting of nucleic acids onto nylon or nitrocellulose membranes. Covalent attachment also may be achieved using pre-synthesized oligonucleotides that are fabricated with a chemical linker at one or both ends of the oligonucleotide. U.S. Pat. No. 6,048,695 to Bradley and Cai discloses a method wherein a linker is added to an oligonucleotide for the purpose of making a covalent bond with reactive moieties on the surface. See e.g. U.S. Pat. No. 6,048,695 and references therein. Thus, oligonucleotide probe attachment occurs with the surface through the linker, rather than by direct adsorptive interaction of the probe with the surface.

Still another means of covalently attaching nucleic acids to a surface is by photolithography. U.S. Pat. No. 5,959,098 to Goldberg et al. discloses a method of derivatizing a surface to provide photoprotected functional groups. Nucleic acids are synthesized directly on the surface by selectively illuminating surface regions to remove the protecting groups. The deprotected regions are then available for covalent attachment of nucleotide monomers having photoprotected functional groups. Repetition of these steps results in oligonucleotides covalently linked to the surface. Further examples of array fabrication include U.S. Pat. No. 6,221,653 to Caren and Luebke (inkjet printing of the nucleic acid building blocks) and U.S. Pat. No. 6,024,925 (microfluidics robot to prepare sample arrays for analysis in a mass spectrometer).

Methods for noncovalently immobilizing nucleic acids typically require a bridging agent. In some cases that bridging agent is a salt or detergent. For example, U.S. Pat. No. 5,610,287 to Nikiforov and Knapp discloses a noncovalent immobilization method comprising contacting a glass or hydrophilic polystyrene solid support with a combination of a nucleic acid and a cationic bridging agent (sodium chloride or a detergent). See e.g. '287, abstract. The method of attachment is based upon interaction of the detergent flocculent with the surface, rather than direct adsorptive interaction between the oligonucleotide and the surface.

Alternatively, the bridging agent may be a high-affinity interaction pair such as avidin and biotin or digoxigenin and an anti-digoxigenin antibody. For example, a biotinylated nucleic acid may be immobilized on a streptavidin-coated surface. See e.g. Belosludtsev Y et al., 2001, *Biochem Biophys Res Commun.* 282:1263-1267; Holmstrom et al., 1993, *Anal. Biochem.* 209(2):278-283. In this method, a biotin-modified linker is added to an oligonucleotide for the purpose of making a bond with avidin or avidin-like groups coated into the surface. Attachment occurs with the surface through the biotin-modified linker, rather than by direct adsorptive interaction of the probe with the surface.

Methods of adsorptive, non-covalent immobilization of long, single or double stranded DNA molecules onto membrane surfaces are the basis for a device referred to as a "Southern" or "Northern" blot. Standard practice of the blotting technology art has shown that, where probe length is less than about 100 bases, the known adsorptive methods of attachment are too weak to support probe attachment that is sufficiently stable to form a hybridization device. Thus, the standard for attachment of short nucleic acid probes in blotting applications has involved covalently crosslinking the nucleic acid to the solid support (as by photochemical cross linking) or other means of non-adsorptive linkage (such as chemical crosslinking). Known methods to increase the strength of adsorptive, non-covalent immobilization of short nucleic acids to membrane supports have been shown to render the DNA unsuitable for a hybridization device and hence the conventional blotting methods involving short nucleic acid probes all employ a covalent means of immobilization. Other types of porous material, including porous beads and related small particle porous substrates, are known to behave as do membranes, that is, long DNA probes may be attached by adsorptive interaction, but short probes must be attached by non-adsorptive means.

Adsorptive, non-covalent immobilization of long, single or double stranded DNA molecules onto non-membranous surfaces, most particularly the planar substrates (often referred to as slides), may be achieved by known methods and used for the fabrication of DNA microarrays. The adsorptive probe interaction is the basis for fabrication and use of DNA microarrays in which long (greater than 100 bases) nucleic acid probes are spotted into planar surfaces to form the microarray. Standard practice of the microarray fabrication art has shown that long nucleic acid probes may be attached to surfaces by means of adsorptive association with polycation-coated surfaces (usually poly-lysine). However when short nucleic acids (less than 100 bases) are to be attached to microarray surface, the known adsorptive methods of microarray attachment are found to be too weak to provide for stable probe attachment to form a microarray-based hybridization device. Thus the standard of the art for attachment of oligonucleotide probes (less than 100 bases) in microarray applications has involved covalent attachment of the nucleic acid to the microarray support, generally by covalent linkage of the oligoncucleotide terminus (3' or 5') to the solid support or other means of non-adsorptive interaction. Known methods to increase the strength of adsorptive, non-covalent immobilization of short nucleic acids to microarray supports have been shown to render the DNA unsuitable for these applications. This may be due to a loss of the ability of the oligonucleotide to form a duplex or unsuitably high levels of non-specific target binding to the microarray.

Oligonucleotides (short single stranded pieces of nucleic acid (DNA, RNA) of less than 100 bases in length) are well suited as probes to be attached to a solid support as the basis for a hybridization device. However, no method is presently known to directly adsorb the oligonucleotide onto a solid support by adsorption, in a way that yields a probe that can be used for hybridization.

In fact, the literature indicates that direct absorption of oligonucleotides is not expected to work. For example, Lindsay asserts that methods of attaching DNA over about 100 bases in length to mica using aminopropyltriethoxysilane for structural analysis by atomic force microscopy result in DNA that is bound too strongly for studies of processes in situ. See Lindsay S M, The Scanning Probe Microscope in Biology, in Scanning Probe Microscopy and Spectroscopy, Dawn A. Bonnell (ed), 2001 by Wiley-VCH, Inc, pg. 289-336.

A recent study of adsorbed oligonucleotides at a hydrocarbon coated silica surface concluded that oligonucleotide (<100 bases) adsorption would necessarily prohibit base pair specific hybridization, and thus make the product useless as a hybridization device. M. J. Wirth states "Any specific adsorption to sites on the surface interferes with the hybridization process. In practice, surfaces tend to have groups that hydrogen bond to the bases on oligonucleotides. Such hydrogen bonding to the substrate gives background noise that reduces the sensitivity of detecting oligonucleotides."

Furthermore, Bradley and Cai argue that adsorptive methods to create DNA hybridization devices adversely affect the quality of performance of the device due to the electrostatic charge on the glass surface. See U.S. Pat. No. 6,048,695, col. 1, line 46 to col. 2, line 8.

Thus, several lines of argument in the literature assert a hybridization device based on direct adsorption of oligonucleotide probes to a solid support is not feasible. To the best of the inventors' knowledge, there is no evidence for or discussion of such an oligonucleotide adsorption based hybridization device described in the literature or available commercially. All known oligonucleotide based hybridization devices (including microarrays, membranes, bead supports and all other configurations involving probe attachment to a support) are based on one of the above-described attachment methods.

SUMMARY OF THE INVENTION

The present invention relates to simple method to fabricate DNA hybridization devices based upon adsorptive rather than covalent attachment of oligonucleotides to a surface. Such adsorbed oligonucleotide probes form a densely packed monolayer, which retains capacity for basepair specific hybridization with a solution state nucleic acid target strand to form the duplex. However, both strand dissociation kinetics and the rate of DNase digestion suggest on symmetry grounds that the target nucleic acid binds to such adsorbed oligonucleotides to form a highly asymmetric and unwound duplex. Thus, a non-helical nucleic acid duplex may be the preferred structural isomer on a charged surface.

The method for forming the novel duplex is shown to be of immediate practical utility, in that it can be implemented at approximately 1/10 the cost of fabrication relative to current alternatives. Hybridization signals are found to be high, due to the dense packing of surface bound probe and selectivity is measured to be at or near the limit already known for hybridization based upon Watson-Crick double helix formation.

The present invention further relates to a device to detect solution state nucleic acid analytes, namely a device comprising a nucleic acid probe that is bound by adsorptive association to the device surface. After adsorptive association to the surface, the bound probe (now on the device surface) is capable of binding to a solution-state nucleic acid target. Such binding may be detected by standard methods including fluorescence, optical, radiometric or potentiometric analysis.

The invention provides working examples of a microarray-based hybridization device based on direct physical adsorption of oligonucleotide probes to a solid support. The device comprises a film of permanent cationic charge at the surface and a linker-free, unmodified oligonucleotide directly adsorbed to the surface. Forces that bind the oligonucleotide to the surface may include electrostatic interactions, hydrogen, bonds, hydrophobic interactions, and combinations thereof. Devices of the invention do not require any intervening or bridging biomolecule between the surface and the oligonucleotide.

Device surfaces of the invention may be hydrophobic or hydrophilic. Hydrophilic device surfaces may be uncharged (polar), negatively charged, or positively charged. The adsorptive force by which the nucleic acid probe is bound to the surface may be selected from the group consisting of hydrogen bonding, electrostatic interactions, Van der Waals interactions, hydrophobic interactions, or combinations thereof.

In some embodiments of the invention, the device surface is smooth and planar (glass, plastic, metal or ceramic). In those instances where the substrate surface cannot engage in direct bonding with the phosphate backbone, the substrate is coated with an appropriate surface film, allowing for the desired adsorptive association. In other embodiments of the invention, the substrate may also be smooth and non-planar, such as a bead constructed of an appropriate substrate material (glass, plastic, metal or ceramic) or a woven textile or paper.

In some embodiments of the invention, the device surface is porous and either planar or non-planar. Pores may be introduced into the device surface as a polymer network, a network of ceramic pores, or by etching of an otherwise-smooth glass, plastic, metal or ceramic surface.

In some embodiments of the invention the device surface is a microarray. In some embodiments of the invention the device surface is a microbead. In some embodiments of the invention the device surface is an electrode. In some embodiments of the invention the device surface is an integrated circuit.

In some embodiments of the invention, the device surface may be used to detect and screen small molecule analytes, based upon their affinity for associating with a probe-target duplex. This may be accomplished by (i) preparing a device comprising a nucleic acid probe that is bound by adsorptive association to the device surface, (ii) exposing the device to a target nucleic acid under conditions which permit formation of the duplex, (iii) exposing the device to a solution of small molecule analytes, and (iv) detecting and/or collecting one or more analytes based on the affinity with which they bind the duplex.

The invention also relates to the small molecule analytes discovered in such a screen and their uses. For example, small molecules that bind to the duplex may be used (i) for optical detection of duplex formation as in devices of the invention or as pharmaceuticals.

The novel, surface bound form of the duplex, which is the basis of the current invention, has a structure which approximates the untwisted, extended, high-energy transition state which is induced by the binding of DNA-specific compounds to an ordinary, Watson-Crick duplex. A device of the invention may be used to screen for compounds that bind with high affinity to the untwisted duplex transition state. These compounds may then be used as leads for subsequent pharmaceutical development or as probe molecules to be used to detect formation of the nucleic acid duplex of the invention.

The invention further relates to a method to detect duplex formation on a device surface, based upon the use of small molecules which bind specifically to a nucleic acid duplex of the invention. A nucleic acid duplex of the invention has structural characteristics, which differ greatly from a standard nucleic acid helix: namely it is greatly untwisted, with an increase of the separation between adjacent base pairs. Thus, compounds capable of binding double helical forms of nucleic acids may display a different affinity for the binding affinity for nucleic acid duplexes of the invention. In particular, dyes and haptins which are capable of intercalating into standard double helical nucleic acid forms may bind to an extended, unwound duplex of the invention with higher affinity than to the double helix. Such compounds could be used to distinguish surface-bound duplex, from a standard double helix which might form in solution as a side reaction during hybridization analysis.

The present invention also relates to methods and devices as described wherein nucleic acid absorption to the surface is via phosphate bonding to a surface coated with a primary amine, a secondary alkyl amine, a tertiary alkyl amine, a guanidinium group, an amidinium group, an imidazolium group, an uncharged organic H-bond donor such as an aldehyde, alcohol or fomamide, an uncharged inorganic H-bond donor such as $SiO_2$, $TiO_2$, $AlO_2$ or others, or combinations thereof.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

DETAILED DESCRIPTION OF THE INVENTION

Figure 1:
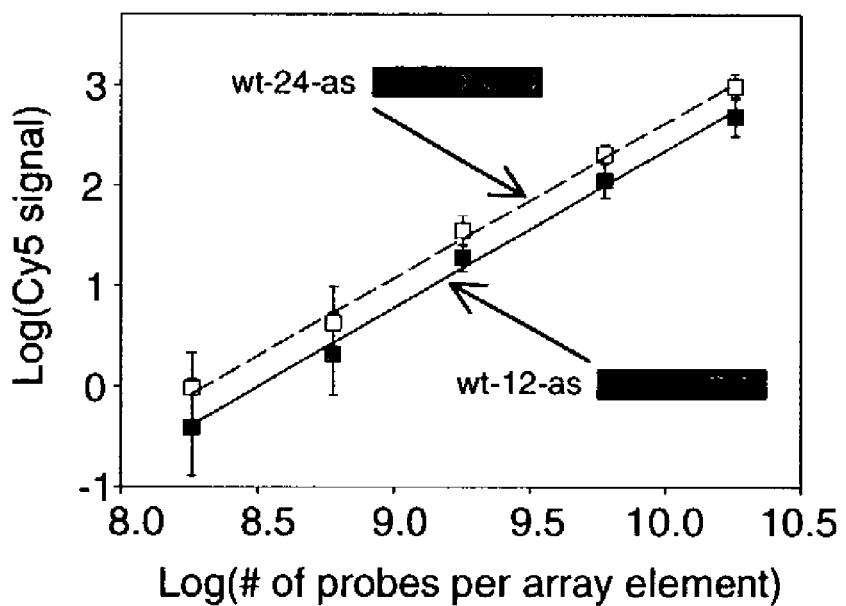
FIG. 1: Non covalent adsorption of DNA oligonucleotides on a positively charged surface. (A) Standard curves for a 12-mer (filled squares) and a 24-mer (open squares). Cy5-labeled probes were printed at 10 nl, then imaged without washing on an ArrayWorx imager (Applied Precision, Inc.). The number of probe molecules per array element, x-axis, was calculated from the product of printed volume, probe concentration, and Avogadro's number. The y-axis represents log of the mean integrated value of Cy5 dye fluorescent signal from the array elements. Each data point represents the mean and a single standard deviation from the mean calculated from 56 array elements. (B) Surface area per oligonucleotide, occupied by a 12-mer (filled circles) or a 24-mer (open circles). Cy5-labeled oligonucleotide probe was printed in 70% DMSO/30% $H_2O$ at 10 nl per array element, as a function of concentration on the aminosilanized glass surface, followed by washing to remove unbound probe. They axis was calculated by dividing the measured array element surface area by the number of adsorbed probe molecules per array element (calculated from standard curves in FIG. 1A). Each data point represents the mean and a single standard deviation from the mean calculated from 56 array elements.
Figure 1:
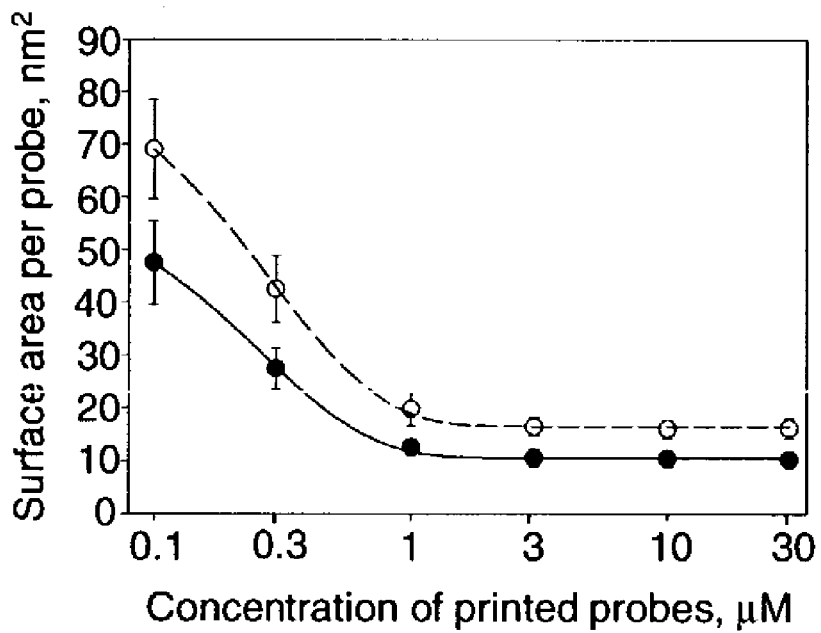

Some of the results presented herein have been published after the filing date of U.S. Provisional Application Ser. No. 60/304,500 (Lemeshko S V et al., 2001, *Nucleic Acids Research* 29(14):3051-3058) the contents of which is hereby incorporated herein in its entirety by reference.

According to the instant invention "adsorb", "adsorption", and grammatical equivalents thereof refer to a noncovalent interaction between a surface and a biomolecule. In preferred embodiments of the invention, the biomolecule is a nucleic acid. In other embodiments of the invention, the biomolecule may be or may comprise one or more amino acids, lipids, and/or carbohydrates. The interaction may be based on electrostatic attraction, hydrogen bonding, Van der Waals interactions, and/or hydrophobic interactions. In presently preferred embodiments, the interaction is based, at least in part, on the electrostatic attraction between the phosphate background and a surface having cationic functional groups.

According to the instant invention "functional group" refers to the atom(s) responsible for the characteristic reactions of a compound. For example, the functional group of alcohols is —OH, the functional group of aldehydes is —CHO, the functional group of carboxylic acids is —COOH. A given functional group behaves in approximately the same way in all molecules of which it is a part. A single molecule may have a plurality of functional groups. Functional groups of the invention mediate a noncovalent interaction between a surface and a nucleic acid According to the instant invention "probe" refers to a nucleic acid, typically single stranded, that is adsorbed to a surface. Probes of the invention may have a length of from about 1 nucleotide to about 100 nucleotides, preferably from about 12 nucleotides to about 60 nucleotides. A nonlimiting model of adsorbed probe structure is that of a nonhelical structure having substantially all backbone phosphate groups contacting the surface.

According to the instant invention "target" refers to a nucleic acid that is either in solution state or hybridized to a probe molecule. Targets of the invention may be single or double stranded and may comprise DNA, RNA or both. In some embodiments of the invention targets may have a length of from about 1 nucleotide to about 100 nucleotides, preferably from about 12 nucleotides to about 60 nucleotides. In some embodiments of the invention, target may have a length of from about 100 nucleotides to full-length cDNAs or mRNAs, preferably mouse or human. A nonlimiting model of a hybridized probe-target structure is that of a nonhelical duplex with a helical pitch angle near zero with at least about 9 of every 10 nucleotides base-paired.

According to the invention, "substrate" refers to any material intrinsically having a surface of the invention. It also refers to any material that may be modified to create a surface of the invention. Substrates may be glass, ceramic, metallic, organic, inorganic or combinations thereof. Substrates may have the form of a slide, a bead or any other form known in the art.

According to the invention, "surface" refers to a covalently-contiguous geometrical domain or a region of a geometrical domain directly contactable by surrounding media and having functional groups that support adsorption of nucleic acids through electrostatic interactions, hydrogen bonding, Van der Waals interactions, London interactions, hydrophobic interactions or combinations thereof. In some embodiments of the invention, a zwitter ionic surface may be used to support biomolecular adsorption. A surface of the invention may be fabricated on a substrate or may be an intrinsic property of the substrate. A nonlimiting example of surface fabrication is aminosilanization of a glass substrate wherein cationic functional groups are covalently linked to the substrate. In some embodiments, a device of the invention is a microarray wherein each spot is a surface as described here.

The present invention provides devices and methods for detecting solution-state target nucleic acids. Devices of the invention comprise a surface and a nucleic acid wherein the nucleic acid is adsorbed to the surface. In some preferred embodiments of the invention, the adsorptive surface is uniform and dense with respect to the functional groups that mediate nucleic acid binding, e.g. polar, uncharged groups, charged groups, hydrophobic groups, and combinations thereof. According to these embodiments, functional group uniformity and density is a critical feature. In some embodiments, the functional group is cationic with a density of about 1 group per 5 Å on center. In some embodiments of the invention, desired functional groups are covalently attached to a substrate to form a surface. In some preferred embodiments, functional groups are attached to the substrate by vapor deposition. A nonlimiting illustrative comparison between the preferred method of vapor deposition of functional groups relative to a prior art solution-dipped method appears in Example 13 and FIG. 8.

In some preferred embodiments, the adsorptive surface is saturated with the oligonucleotide forming a monolayer to maximize probe retention. This may be accomplished by applying about two fold more probe to the surface than required. In a nonlimiting hypothetical example, a probe concentration of 10 μM is used where a titration curve (such as displayed in FIG. 1) indicates that the amount that probe required for saturation is 5 μM.

In some preferred embodiments, capping residual surface charges following probe adsorption is essential. The invention contemplates the use of any means of capping known in the art. In some embodiments chemical capping may be used. In other embodiments capping may be achieved with a surfactant (e.g. SDS).

The present invention further relates to a method for adsorbing a nucleic acid on to a surface comprising contacting a surface with a saturating amount of nucleic acid under conditions that permit adsorption and capping residual nucleic acid binding sites wherein said surface has uniformly distributing functional groups that support adsorption. In some embodiments, the method further comprises covalently modifying the surface with desired functional groups.

The present invention also relates to a novel composition of matter, namely a new stable form of a nucleic acid duplex. The data presented here suggest that single-stranded DNA can bind tightly to a positively charged, aminosilanized glass surface to form a densely packed nucleic acid monolayer. Upon sequence-selective hybridization of such adsorbed probes to their antiparallel Watson-Crick complement, a duplex is formed with distinctly asymmetric properties that appear hard to reconcile with the known helical DNA structures, such as A, B, or Z double helix. Throughout the instant application, the term "duplex", unless otherwise indicated, refers to this nucleic acid form which is characterized by a reduction of helical pitch angle to a value near to zero. This new form is created by adsorptive binding to a surface of the phosphate backbone of a DNA or RNA single strand "probe", greater than 10 bases in length, followed by Watson-Crick base pairing (A-T, C-G) of a cognate RNA or DNA strand "target" to form the unwound, surface-bound probe-target duplex.

Although unexpected in a simple, mixed phase hybridization experiment as presented here, it is interesting to note that unwound ribbon-like duplexes have been proposed to exist transiently in other somewhat more extreme contexts. For instance, the DNA complex formed upon binding of intercalators such as ditercalinium, as revealed by X-ray crystallography (Gao O et al., 1991, *Proc. Natl. Acad. Sci. USA* 88:2422-2426), involves a nearly complete loss of helical winding. Similarly, an unwound and significantly extended double helix has been proposed to form in solution as a response to the mechanical stress induced by stretching (Leger J F et al., 1999, *Phys. Rev. Lett.* 83:1066-1069; Bensimon D et al., 1995, *Phys. Rev. Lett.* 74:4754-4757; Smith S B et al., 1996, *Science* 271:795-799; Lebrun A et al., 1996, *Nucl. Acids Res.* 24:2260-2267).

Within the context of an antiparallel double helix, it is well known that base stacking and helix twist are coupled mechanically. In the studies described previously, either a chemical force (insertion of a heterocycle between base planes) or mechanical strain upon the duplex (stretching) is coupled to an increase of base pair separation and a resultant loss of helical twist.

Figure 3:
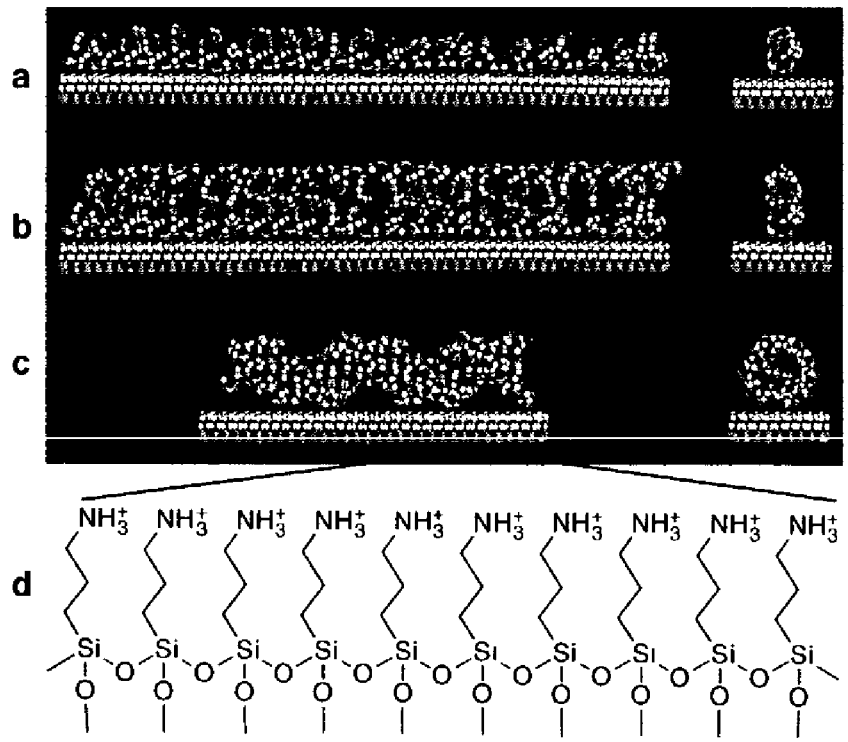
FIG. 3. Models of duplex formation on a cationic surface of the invention. (A) Single-stranded, 24-mer oligonucleotide probe electrostatically attached to an aminosilanized surface. (B) A linear, non-helical DNA ribbon duplex on a cationic surface of the invention, formed along its full length between an extended 24-mer probe and its 24-mer complementary target. (C) A 24 base pair long B-form DNA double helix on a cationic surface of the invention. (D) The chemical structure of a 3-aminopropyltrimethoxysilanized glass surface of the invention. The models in FIGS. 3A-C were generated in the Molecular Builder module of InsightII and energy minimizations for ribbon duplex structure were done with the Amber force field of Discover 3 package (MSI). Although it is quite possible that most common isomers of single-stranded (FIG. 3A) and double-stranded (FIG. 3B) DNA may have some curvature on a positively charged surface, only the linear isomers are shown for simplicity.

The experimental data described here do not measure base pair separation directly. However, as previously predicted from modeling studies, these inventors have found it difficult to generate adsorbed linear, ribbon-like duplexes that do not involve at least a 50% increase in duplex length relative to the B-helix (FIG. 3B). Thus, it is interesting to consider that the ribbon-like duplex, which has been inferred from studies described here, may have necessarily incurred a significant loss of base stacking due to stretching. It is well known that the energetics of duplex formation is mainly determined by base stacking interactions and electrostatic repulsion among phosphates (Dickerson R E, 1992, *Methods Enzymol.* 211:67-111; McConnell K J et al., 2000, *J. Mol. Biol.* 304:803-820).

The methods and devices of the invention provide several advantages over prior art methods and device. For example, the methods and devices of the invention do not require nucleic acid derivitization with a linker thereby eliminating the inefficiencies and costs associated with such a step. Possible inefficiencies of existing methods include incomplete derivitization of the nucleic acid with the linker, biased derivitization of some nucleotide sequences over others, incomplete association of the linker to the surface, and necessary additional manufacturing step(s). A further advantage over the covalent methods of attachment is the reversibility of the probe-surface bond. In some embodiments, the invention provides a method for identifying the nucleotide sequence to which a nucleotide binding protein (e.g. a transcription factor) binds comprising contacting a microarray having surface-bound probe-target duplexes with a nucleotide binding protein under conditions that permit binding of at least one duplex to said protein, eluting duplex-protein complexes from the surface (e.g. with a concentrated salt solution), and sequencing at lest one strand of said duplex.

The findings illustrated in the Examples suggest that due to the direct and indirect consequences of duplex adsorption upon a plane, both the structure and the energetics of ribbon-like duplex formation differ from that known in dilute aqueous solution. The practical applications of such structural and energetic differences are significant:

The Novel Duplex Form Mimics a Transition State. The binding of drugs and proteins to the double helix often is associated with transient formation of an extended, unwound form of the double helix. The data presented here show that in most respects, the novel helix form described here mimics such a transition state. Potent drugs have been developed based upon their ability to bind to the transition state of the substrate-enzyme complex (so-called transition state analogues). By analogy, the use of the novel duplex form described here (in the context of appropriate devices and methods) allows such DNA transition state analogues to be discovered as pharmaceutical lead compounds.

The Novel Duplex Form Has Enhanced H-Bonding Selectivity. The data presented show that base pairing selectivity in the novel duplex form meets or exceeds that seen in the standard Watson-Crick duplex. Molecular modeling of the novel duplex form suggests that base stacking (which is not very sequence dependent) is greatly reduced in magnitude relative to the energy of H-bonding (which is the basis for nucleic acid sequence selectivity). Thus, both modeling and experiment suggest that methods and devices based upon the novel, untwisted duplex will display more precise base sequence recognition than can be attained with the double helix.

Close Proximity to the Surface Allows for Modulation of Hybridization. The formation of the novel untwisted duplex form is driven by the symmetry constraints associated with surface adsorption. Thus, at its core, the novel duplex form is a molecular entity with structure and energetics that are intimately coupled to the physical chemistry of the surface. As illustrated in the Examples, when the surface is cationic, the electrostatic component of the duplex-surface interaction can eliminate the ordinary requirement for cations in the hybridization solution. This observation reduces to practice the concept that the ionic dependence, temperature dependence and selectivity of hybridization (to form the novel duplex) can be modified greatly by judicious surface modification.

Both Cationic and Non-Cationic Surfaces will Support the Novel Duplex Form. In the data presented, the underlying substrate was primary amine coated glass. Thus, nucleic acid probe adsorption to the substrate is based upon a combination of electrostatic and H-bonding interaction between the amino groups and the phosphate backbone. Experimental data and modeling suggest that the novel helix form requires stable adsorption mediated through the phosphate. Electrostatic interaction between the negatively charged phosphate and the underlying surface should be sufficient to achieve stable adsorption of that kind. Thus, charged surface coatings of all kinds (e.g. primary, secondary, tertiary amines, amidinium and guanidinium groups, and metal ions) may support the novel surface form. At the other extreme, since phosphate is also an excellent H-bond acceptor, neutral H-bond donating surfaces may also be capable of supporting formation of the novel helix form: this includes, inter alia, hydroxyl, amide, urea and other good metallic H-bond donors such as $AlO_2$, $TiO_2$ and $SiO_2$.

EXAMPLES

The following examples are presented for illustration purposes only and in no way limit the various embodiments that fall within the scope of the invention.

Example 1

Aminosilanization of a Glass Surface

Glass, pre-cleaned, micro slides (Gold Seal, Gold Seal Products) were cleaned in deionized water, followed by rinsing in HPLC-grade methanol and dried in dust-free oven at 45 C. The slides were transferred to a vacuum oven at 82 C, equilibrated against 3-aminopropyltrimethoxysilane (Aldrich) in 1:2 proportion to p-xylene (Aldrich). The slides were then incubated overnight at 27 mm Hg, followed by storage at room temperature under dust free conditions.

Example 2

Fabrication of Arrays

All oligodeoxyribonucleotides were synthesized, labeled with Cy3 or Cy5 fluorescent dyes at the 5'-ends, and HPLC purified by BioSource International (Camarillo, Calif.). A Microlab 4200 robot (Hamilton) with 10 µl syringes was used to print 6×8 arrays on aminosilanized glass slides: 10 nl volume per array element, 500 µm diameter, 900 µm center to center. Oligodeoxyribonucleotides were printed from 384 well plates (NUNC) at the desired concentration in 70% DMSO (Aldrich)/30% $H_2O$. DMSO inclusion in the printing solution slowed the process of drying and therefore resulted in more uniform probe density within the array elements as compared to printing the probes in water. After printing, arrays were washed in 10 mM NaOH, 100 mM Na+ carbonate, 2% polyvinyl alcohol, 5× Denhardts for 1 min, then rinsed multiple times in deionized $H_2O$, and dried for storage. All procedures were performed at room temperature.

Example 3

Hybridization and Imaging

Hybridization was carried out in the following hybridization buffers: 90 mM Na+ carbonate, 5× Denhardts, pH=9.5 for 12-mer targets and 60 mM Na+ carbonate, 5× Denhardts, 20% formamide, 0.6% polyvinyl alcohol, pH=9.5 for 24-mer targets. The pH has been held at 9.5 throughout in order to reduce surface charge due to free amino groups. Before hybridization, the arrays were pretreated in corresponding hybridization buffers without the targets, containing 1.5% (w/v) polyvinyl alcohol (Aldrich), used as a blocking agent. All steps were done at room temperature. After 10 minutes of hybridization, the slides were washed in corresponding hybridization buffers, rinsed several times in deionized water, dried, and imaged. The arrays were imaged on a CCD based Arrayworx Imager (Applied Precision, Inc.) with 10 µm resolution. Cy3 and Cy5 optical filters were used during the imaging of the arrays. Exposure times were held at 0.2 sec for Cy3 channel and 1 sec for Cy5 channel, in order to normalize sensitivity. The analysis of intensities from Cy3 and Cy5 channels was done in ArrayWoRx Version 1.50 software (Applied Precision, Inc.) from the original stitched images and the bar graphs were generated in Microsoft Excel. The pictures of the representative arrays were modified by adjusting the levels in Adobe Photoshop 5.5 for presentation purposes only, and the level adjustments did not have any effect on conclusions, since the quantification was done based on the original images.

Example 4

Calculation of Target to Probe Ratio

For these experiments, it was important to have a high target to probe ratio, therefore 12-mer targets were hybridized at 5 µM concentration, and 24-mer targets were hybridized at 3 µM concentration, unless stated otherwise. Time course and concentration dependence experiments have revealed that at such concentrations of the targets their signal was saturated on specific probes after 5 minutes of hybridization. The target to probe ratio has been measured based on calculation of the number of molecules from the analysis of Cy5 signals before hybridization for probes, Cy3 signals after hybridization for targets, and standard curves for Cy3- and Cy5-labeled oligodeoxyribonucleotides (FIG. 1a). The standard curve for Cy5-wt-24-as (n=56) was fit by a linear regression (log(Cy5 signal)=yo+a*log(number of molecules)) in Sigma Plot 2000. The number of molecules was found from the known volume (10 nl per array element) and concentration of oligodeoxyribonucleotide in printed solution per array element. The standard curves for Cy3-wt-24-s (n=56) and Cy3-wt-12-s (n=56) were fit by a linear regression (log(Cy3 signal)=yo+a*log(number of molecules)) in Sigma Plot 2000. The regression curve for Cy5-wt-24-as probe had values yo=-13.1, a=1.58, R=0.999, where R is the regression coefficient of the mean. The regression curves for the targets Cy3-wt-24-s and Cy3-wt-12-s had values yo=-9.69, a=1.29, R=0.997 and yo=-13.7, a=1.64, R=0.999, respectively. The average background subtracted Cy5 signal of Cy5-wt-24-as probe before hybridization was 332.

Thus the number of Cy5-wt-24-as probe molecules per array element could be calculated from its regression equation: (probe number of molecules)=$10^{[(log(Cy5\ signal)-yo)/a]}$=$10^{[(log(332)+13.1)/1.58]}$=$7.7*10^9$. In the same way, the number of target molecules after hybridization was found to be $3.8*10^9$ for Cy3-wt-24-s and $7.8*10^9$ for Cy3-wt-12-s. Thus the target to probe ratio was 0.5 and 1 for 24 and 12 bases long targets hybridization to 24 bases long probes, respectively. The concentration of 24 bases long targets was not increased above 3 µM, because that would lead to dramatic increase in background. The fact that 5 µM concentration could be used for 12 bases long targets could be explained by the fact that longer nucleic acids have more negative charge and therefore are attracted stronger to a positively charged surface. The ability of the adsorbed onto the positively charge surface oligodeoxyribonucleotide probes to specifically hybridize to nucleic acid targets with target to probe ratio approaching 1 has been shown previously by radioactive labeling of the targets (Belosludtsev Y Y et al., 2001, *Anal. Biochem.* 292:250-256).

Example 5

Dissociation Experiments

After hybridization, the slides were washed 5 times in the corresponding hybridization buffer containing 1.5% (w/v) polyvinyl alcohol. They were then incubated for various times at room temperature in the wash buffer containing 60 mM Na+ carbonate, 20% formamide for 12-mers and 35% formamide for 24-mers, 5× Denhardts, 0.6% polyvinyl alcohol, pH=9.5.

Example 6

DNase Protection Assays

After hybridization, the slides were washed two times in corresponding hybridization buffer containing 1.5% (w/v) polyvinyl alcohol, followed by brief application of the DNase I digestion buffer containing 50 mM KCl, 10 mM $MgCl_2$, 20 mM Tris-HCl, pH=8.0. The slides were then incubated for 20 min at room temperature in 0, 0.1, 1.0, or 10 u/µl of DNase I (Roche) in the buffer above, rinsed 8 times in corresponding hybridization buffer containing 1.5% polyvinyl alcohol, then washed in deionized water, dried and imaged.

Example 7

Adsorption of Oligodeoxyribonucleotides to Aminosilanized Glass Surface

Cy5 (indodicarbocyanine, $\lambda(ex)_{max}$=651 nm, $\lambda(em)_{max}$=651 nm, red) dye-labeled 12 bases long (12-mer) and 24-mer oligodeoxyribonucleotide (oligonucleotide) probes were printed on an aminosilanized glass surface (3-aminopropyltrimethoxysilane) in the array format. Unadsorbed material was removed by extensive washing at room temperature. The bound Cy5 oligonucleotide signal was saturated beginning at 1 µM of the printed oligonucleotide. By reference to standard curves (FIG. 1A) the surface area per bound oligonucleotide could be calculated as a function of total applied probe concentration. A well-defined density limit was detected (FIG. 1A) for both 12-mer and 24-mer probes. At saturation, it was found that 10.6±0.3 $nm^2$ is occupied by a Cy5-labeled 12-mer oligonucleotide and 16.6±0.5 $nm^2$ is occupied by a Cy5 labeled 24-mer oligonucleotide. Assuming a 1 nm width for an oligonucleotide strand and full extension of the phosphate backbone (at 0.7 nm per base repeat) it is predicted that a 12-mer or 24-mer should occupy approximately 7.7 $nm^2$ or 16.1 $nm^2$ of surface, respectively. The appended dye label might be expected to add 1 $nm^2$ to that. Thus, the data suggest that at adsorptive binding saturation, surface structure for both 12-mer and 24-mer probe approximates a densely packed monolayer of extended probe oligonucleotide strands.

Adsorptive attachment of such labeled oligonucleotides was found to be slowly reversible, probes remaining bound to the surface even after repeated washing with boiling deionized water. The adsorbed oligonucleotides could be removed by washing with boiling 5 M NaCl, indicating reversible non-covalent electrostatic interaction. Thus, the attachment of oligonucleotides to the surface can be attributed to extremely tight electrostatic interaction of the negatively charged phosphate backbone of nucleic acids to the positively charged amine groups of the surface.

Example 8

Specific Hybridization of DNA to Adsorbed Oligonucleotides

To determine whether DNA could specifically hybridize to such a densely adsorbed oligonucleotide monolayer, microarrays were fabricated with six Cy5-labeled DNA oligonucleotide probes (red), printed in quadruplicate on the aminopropylsilane surface, slightly below saturation of probe adsorption (0.3 µM of added probe) and also at a saturating probe concentration of 3.0 µM. For 12-mer probes (left side of arrays in FIG. 2) and 24-mer probes (right side of arrays FIG. 2) three probe sequence homologues were employed: a wild-type reference sequence (wt), a single nucleotide change per 12 bases (mt), and the randomly scrambled isomer (scr). Sequences are provided in Table 1.

Microarrays were hybridized to a Cy3 (indocarboxysyanine, $\lambda(ex)_{max}$=552 nm, $\lambda(em)_{max}$=565 nm, green) labeled 12-mer target (FIG. 2B) or 24-mer oligonucleotide target (FIG. 2C), chosen to be complementary to the wild-type reference probe sequence. Hybridization was performed at a relatively high solution state target concentration (3 µM for 24-mer targets and 5 µM for 12-mer targets) to achieve saturation of the perfectly matched duplex binding equilibrium (yellow). At the saturation point, the bound target to probe ratio in these hybridization experiments has been measured to be 0.5 for 24-mer targets and 1 for 12-mer targets (see materials and methods). Thus, specificity data obtained comprise a representative average over the entire adsorbed probe monolayer.

Note that the 12-mer target (FIG. 2B) was designed to be complementary to both the wild type 12-mer and a segment of the 24-mer probe strands. Similarly, the 24-mer target (FIG. 2C) was designed to be complementary to both the wild type 24-mer probe and (with target strand overhang) to the 12-mer wild type probe strands. However, for the 24-mer target hybridization, experimental stringency has been increased so that binding to the 12-mer probe is too weak to be detectable (FIG. 2C, left side).

Visual inspection of the data reveals that, even at binding saturation, hybridization is highly specific. A single base mismatch in a 12-mer pairing, or two mismatches in a 24-mer pairing are seen to produce more than a 5-fold reduction of target binding (compare rows 2 and 4 in FIGS. 2B and 2C), while binding to the scrambled isomer cannot be detected. Thus, the data above have confirmed that oligonucleotides bound by adsorption to an aminosilanized surface retain the capacity to bind their antiparallel Watson-Crick sequence complement with measurable single mismatch discrimination within a 12-mer duplex and double-mismatch discrimination within a 24-mer pairing. Hybridization of the targets complementary to mt probes, as well as reversal of the targets and the probes additionally support this conclusion.

Example 9

Formulation of the Symmetry Argument for a Helical Duplex

Strong, nearly irreversible adsorption of a single-stranded DNA oligonucleotide to a positively charged, aminosilanized surface suggests multiple electrostatic interactions between backbone phosphate groups and the surface, as depicted in FIG. 3A. The aminosilane monolayer presents to solution a plane of closely packed amine groups (FIG. 3D). During formation of a rotationally symmetric double helix with an ordinary 10 base pair pitch (FIG. 3C), the ribbon-like phosphate backbone of the probe (FIG. 3A) must detach from that densely charged surface, transiently, in order to wrap about the incoming target strand. In contrast, probe desorption from the surface is not required to explain formation of a non-helical duplex, such as that depicted in FIG. 3B.

If the duplex formed on the surface were a helix, with a relatively ordinary pitch, helical symmetry requires that both strands (target and probe) bind equally to the surface through their rotationally equivalent phosphate backbones (FIG. 3C); and thus, during the process of duplex dissociation, it would be impossible to remove the target without concomitant dissociation of the symmetrically equivalent probe strand. In view of the simplicity of the modeling technique and the substantial uncertainty of surface forces, the models of FIG. 3 should be treated as an approximation.

TABLE 1

Cy3- and Cy5-labeled oligodeoxyribonucleotides (Biosource International) were used in the experiments.

| Oligodeoxyribo-nucleotide name | Oligodeoxyribonucleotide sequence, 5' to 3' | 5'-label | Color | Probe (P) or Target (T) | SEQ ID NO. |
|---|---|---|---|---|---|
| wt-12-as | ctgtagtgggcg | Cy5 | red | P | 1 |
| mt-12-as | ctgtagagggcg | Cy5 | red | P | 2 |
| scr-12-as | gtcgtggagcgt | Cy5 | red | P | 3 |
| wt-24-as | ctgtagtgggcgtcctgctgttcc | Cy5 | red | P | 4 |
| mt-24-as | ctgtagagggcgtccagctgttcc | Cy5 | red | P | 5 |
| scr-24-as | tggtgcggtgacaagctcctcctg | Cy5 | red | P | 6 |
| wt-12-s | cgcccactacag | Cy3 | green | T | 7 |
| mt-12-s | cgccctctacag | Cy3 | green | T | 8 |
| scr-12-s | acgctccacgac | Cy3 | green | T | 9 |
| wt-24-s | ggaacagcaggacgcccactacag | Cy3 | green | T | 10 |
| mt-24-s | ggaacagctggacgccctctacag | Cy3 | green | T | 11 |
| scr-24-s | caggaggagcttgtcaccgcacca | Cy3 | green | T | 12 |
| wt-10-s-(-3') | cgcccactac | Cy3 | green | T | 13 |
| wt-10-s-(-5') | cccactacag | Cy3 | green | T | 14 |
| wt-11-s-(-3') | cgcccactaca | Cy3 | green | T | 15 |
| wt-11-s-(-5') | gcccactacag | Cy3 | green | T | 16 |
| wt-14-s | gacgcccactacag | Cy3 | green | T | 17 |
| wt-16-s | aggacgcccactacag | Cy3 | green | T | 18 |
| wt-18-s | gcaggacgcccactacag | Cy3 | green | T | 19 |
| wt-20-s-(-3') | aacagcaggacgcccactac | Cy3 | green | T | 20 |
| wt-20-s-(-5') | cagcaggacgcccactacag | Cy3 | green | T | 21 |
| wt-22-s-(-3') | ggaacagcaggacgcccactac | Cy3 | green | T | 22 |
| wt-22-s-(-5') | aacagcaggacgcccactacag | Cy3 | green | T | 23 |
| wt-28-s | caggaacagcaggacgcccactacagtt | Cy3 | green | T | 24 | s, sense;
as, antisense;
wt, wild type;
mt, mutant type;
scr, scrambled or random;
the number in the name is the number of bases.

Example 10

Figure 2:
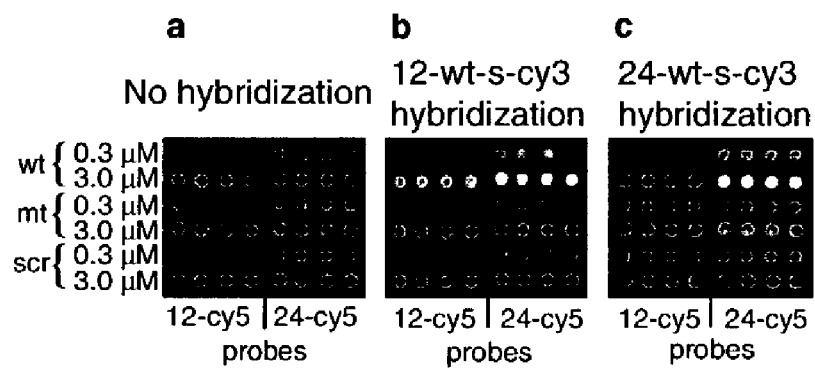
FIG. 2: Fabrication of the arrays and specific hybridization. (A) A prototype of the layout of a microarray of the invention. (B) Hybridization of a 12-mer Cy3-labeled target to the array shown in FIG. 2A. A 10 minute hybridization at 5 μM and at room temperature was followed by a 1 min wash at room temperature in 60 mM Na+ carbonate, 20% formamide, 0.6% polyvinyl alcohol, 5× Denhardts, pH=9.5. (C) Hybridization of a 24-mer Cy3-labeled target to the array shown in FIG. 2A. A 10 minute hybridization at 3 μM and at room temperature was followed by a 1 min wash at room temperature in 60 mM Na+ carbonate, 35% formamide, 0.6% polyvinyl alcohol, 5× Denhardts, pH=9.5. Hybridization conditions are described in materials and methods. Probe and target sequences are described in Table 1. Cy3 signal is green and Cy5 signal is red.
Figure 4:
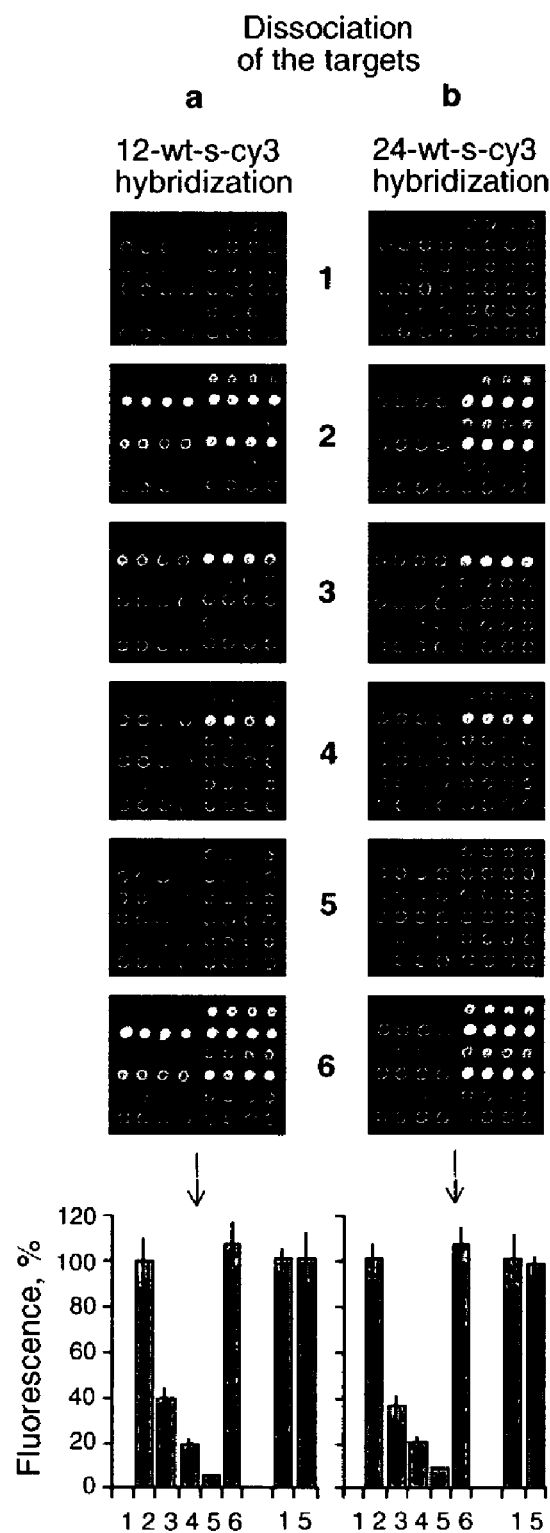
FIG. 4. Dissociation kinetics to analyze strand asymmetry within the surface-bound duplex. (A) Wild type sense 12-mer targets labeled with Cy3 dye hybridized to the arrays described in FIG. 2. (B) Wild type sense 24-mer targets labeled with Cy3 dye hybridized to the arrays described in FIG. 2. The kinetics of target dissociation during washing: (1) no hybridization, (2) after hybridization and no dissociation, (3) after hybridization and dissociation for 1 min, (4) after hybridization and dissociation for 4 min, (5) after hybridization and dissociation for 16 min, (6) after hybridization and dissociation for 16 min, followed by a second hybridization step. The bar graphs represent the normalized means and the standard deviations of the mean from eight array elements.

Asymmetric Dissociation of the Strands from the DNA Duplex Formed on Aminosilanized Glass Surface Such experimental dissociation analysis is shown in FIG. 4, which depicts a dissociation kinetics experiment similar in form to the equilibrium binding experiment of FIG. 2. Briefly, a Cy3-labeled 12-mer target (left) or a Cy3-labeled 24-mer target (right) was hybridized to microarrays of Cy5-labeled oligonucleotide probes as described in FIG. 2. Target was then dissociated from the probes by stringent washing as a function of time. At each time point, binding signals were quantified fluorimetrically by deconvoluting the signal from the bound duplex (yellow) into its two components: Cy3 target (green) and Cy5 probe (red).

Comparison of the initial and final dissociation time points (FIG. 4, array 2 vs array 5 and subsequent bar graphs), reveals that during 16 minutes of washing, the target strand of both the 12-mer and 24-mer duplex pairings is greater than 90% dissociated from the microarray, under conditions which have left the density of adsorbed probes intact (compare array 1 vs array 5 and subsequent bar graphs). Moreover, a repeat of hybridization upon an array, which had been previously hybridized and then washed for 16 minutes (array 6) reveals that the process of hybridization and dissociation is fully reversible, thereby confirming that probe has not been lost or otherwise altered structurally during the course of duplex formation and dissociation. Again, since the initial ratio of bound target to probe has been measured to be close to 1 in these experiments, one may conclude that the observed kinetic asymmetry during dissociation is a general property of all duplex pairings formed on the microarray surface.

This highly asymmetric kinetic behavior is not easily rationalized in the context of a helical structure for the surface bound duplex, since in that case the targets would be bound to the surface in a manner equivalent to probe strands (FIG. 3C). To confirm that important experimental observation, a 3 mm$^2$ area of the aminosilanized glass surface was saturated with the same set of three Cy5-labeled 12-mer and 24-mer probes (wt, mt, scr) described for microarray analysis. Cy3-labeled complementary targets (green) were hybridized to this patch of adsorbed probe under conditions identical to those described for microarray analysis in FIG. 4 and imaged. The surface was then rinsed briefly in hybridization buffer (to remove unbound target), followed by application of the wash buffer to initiate dissociation of the duplex, as described previously for microarray analysis. FIG. 5A presents those image data. The first row presents raw image data for 1 mm$^2$ of the probe-modified surface monolayer prior to hybridization; the second row presents 1 mm$^2$ of the same surface after hybridization to target binding saturation; and the third row presents 1 mm$^2$ of the surface after hybridization and then a 15-minute wash. Overall, bulk analysis of surface hybridization in FIG. 5A (rows one-three) directly confirms the specificity and kinetics of dissociation that had previously been monitored in the microarray format.

Figure 5:
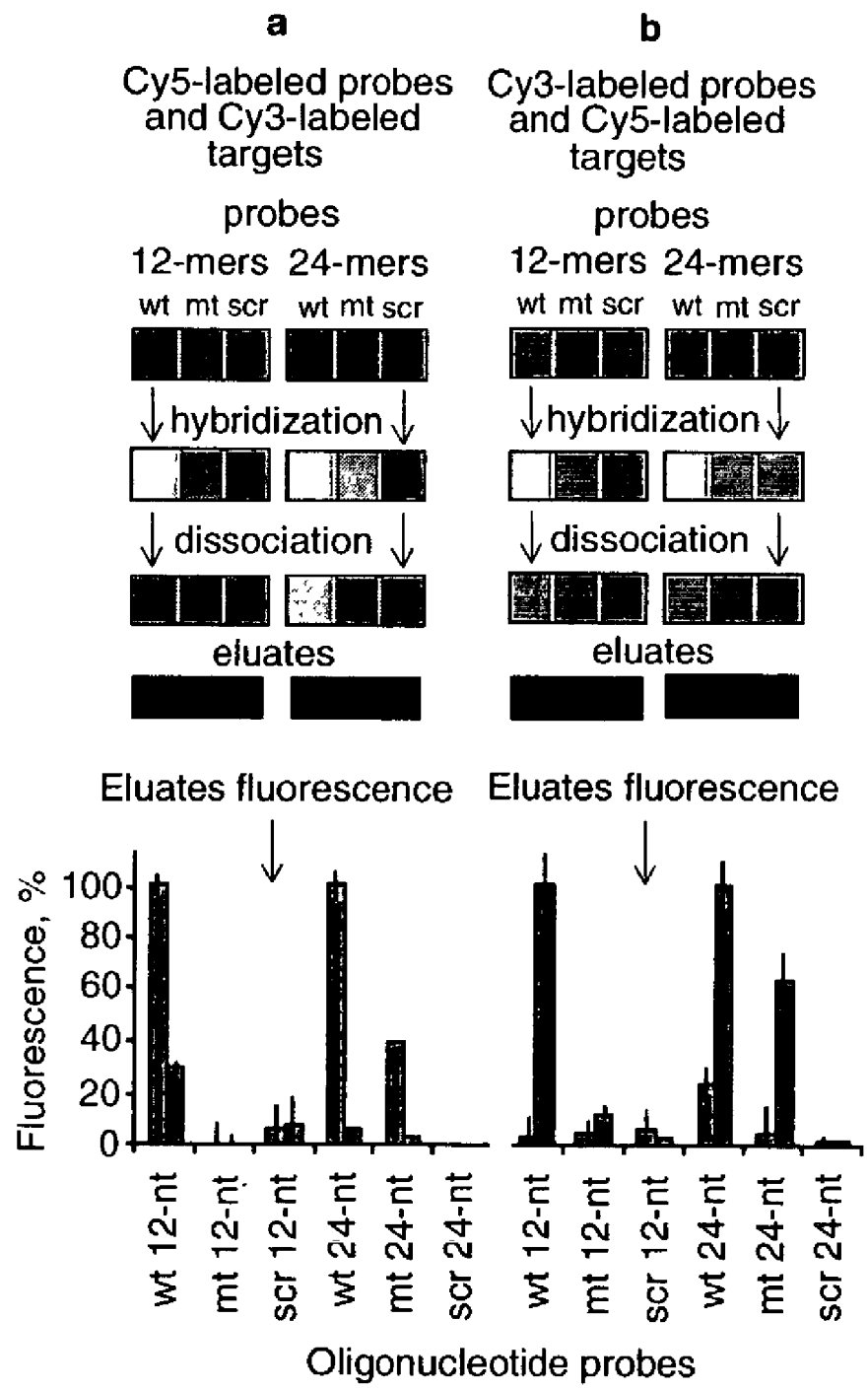
FIG. 5. Analysis of the washing eluate. (A) Patches of aminosilanized surface (3 mm² each) were saturated with Cy5-labeled probes (red), followed by rinsing to remove the excess probes as described in materials and methods. Cy3-labeled targets (green) were hybridized to these patches, rinsed to remove the unbound targets, and washed in 2 μl of the washing buffer for 15 min (see materials and methods). A 0.2 μl aliquot was aspirated from the resulting washing buffer and spotted on a clean slide, which was subsequently imaged with Cy3 and Cy5 filter sets on the ArrayWorx Imager (Applied Precision). (B) The reverse experiments are also shown where the targets and the probes have been reversed. The bar graphs represent the normalized means and the standard deviations of the mean from four such 0.2 μl eluates.

After 15 minutes of dissociation, the wash buffer was collected and pipetted onto a clean aminosilanized glass slide and imaged. Those raw image data are presented in row four. Strong Cy3 and weak Cy5 signals are obtained (FIG. 5A). When the experimental protocol was reversed and probes were used as solution state targets and targets were used as surface bound probes, the result was reversed, i.e. the wash buffer contained strong Cy5 and weak Cy3 signals (FIG. 5B) in relative proportion, which is generally the inverse the distribution obtained in the initial analysis. Overall, the data of FIG. 5 confirm a 5-20 fold kinetic asymmetry for dissociation of the two surface bound duplex strands.

Example 11

Figure 6:
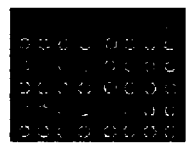
FIG. 6. DNase protection assays according to Example 6. (A) Wild-type, sense, Cy3 dye labeled 12-mer targets hybridized to the arrays described in FIG. 2. (B) Wild-type, sense, Cy3 dye labeled 24-mer targets hybridized to the arrays described in FIG. 2. (1) No hybridization, (2) after hybridization and incubation with 0 u/μl of DNase I in DNase buffer, (3) after hybridization and incubation with 0.1 u/μl of DNase I, (4) after hybridization and incubation with 1.0 u/μl of DNase I, (5) after hybridization and incubation with 10.0 u/μl of DNase I, (6) after hybridization, incubation with 10.0 u/μl of DNase I, prehybridization and second hybridization. The bar graphs represent the normalized means and the standard deviations of the mean from 8 array elements. Cy3 signal is green and Cy5 signal is red.
Figure 6:
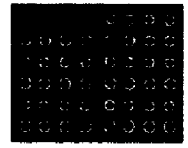
Figure 6:
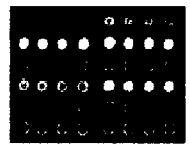
Figure 6:
Figure 6:
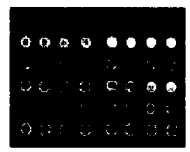
Figure 6:
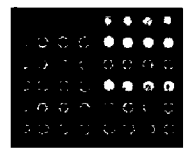
Figure 6:
Figure 6:
Figure 6:
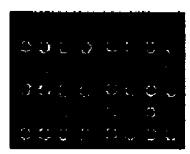
Figure 6:
Figure 6:
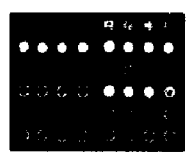
Figure 6:
Figure 6:
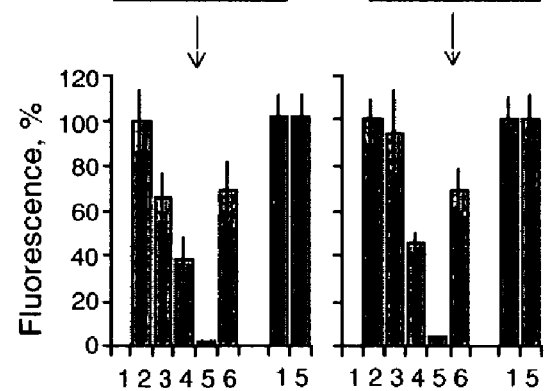

Asymmetric DNase I Digestion of the Strands from the DNA Duplex Formed on Aminosilanized Glass Surface In order to confirm the observed strand asymmetry by a third method, the surface bound duplex was analyzed by quantitative DNase I digestion (FIG. 6). Briefly, the experiment was designed exactly as in FIG. 4, but rather than being monitored for dissociation kinetics, bound duplexes were digested at room temperature for 20 min as a function of increasing DNase I concentration (arrays 2-5 comprising 0, 0.1, 1.0 & 10 units of DNaseI, respectively). As seen by direct comparison (array 1 vs array 5) fluorescence signals from the adsorbed probe strands are completely protected from DNase I cleavage (presumably due to the direct phosphate backbone interaction with surface amines), under conditions in which greater than 90% of the bound 12-mer (FIG. 6A) or 24-mer (FIG. 6B) target strands were digested away with DNase I. However, re-hybridization of arrays which had been previously digested at the highest DNaseI concentration (compare array 2 vs array 6) suggests a small but finite loss of probe capacity to bind target, which may reflect a slow but finite rate of probe cleavage by DNase I, which does not appear to alter probe association with the surface, as detected by fluorescence.

When a standard B-form double helix is formed in solution first and then deposited on the surface, it is well known that DNase I digests both strands symmetrically (Rhodes D et al., 1980, *Nature* 286:573-578). Thus, the pattern of highly asymmetric DNase I protection detected in this study has confirmed the idea that the phosphate backbone of adsorbed probe strands is not available for interaction with solution state DNase I, but instead faces the aminosilanized surface. On the other hand the data confirm that the phosphate backbone of the bound target strand faces the solution phase and remains readily accessible to DNase digestion.

Example 12

Duplex Forms Along the Length of More Than Two Helical Turns of B-Helix

Figure 7:
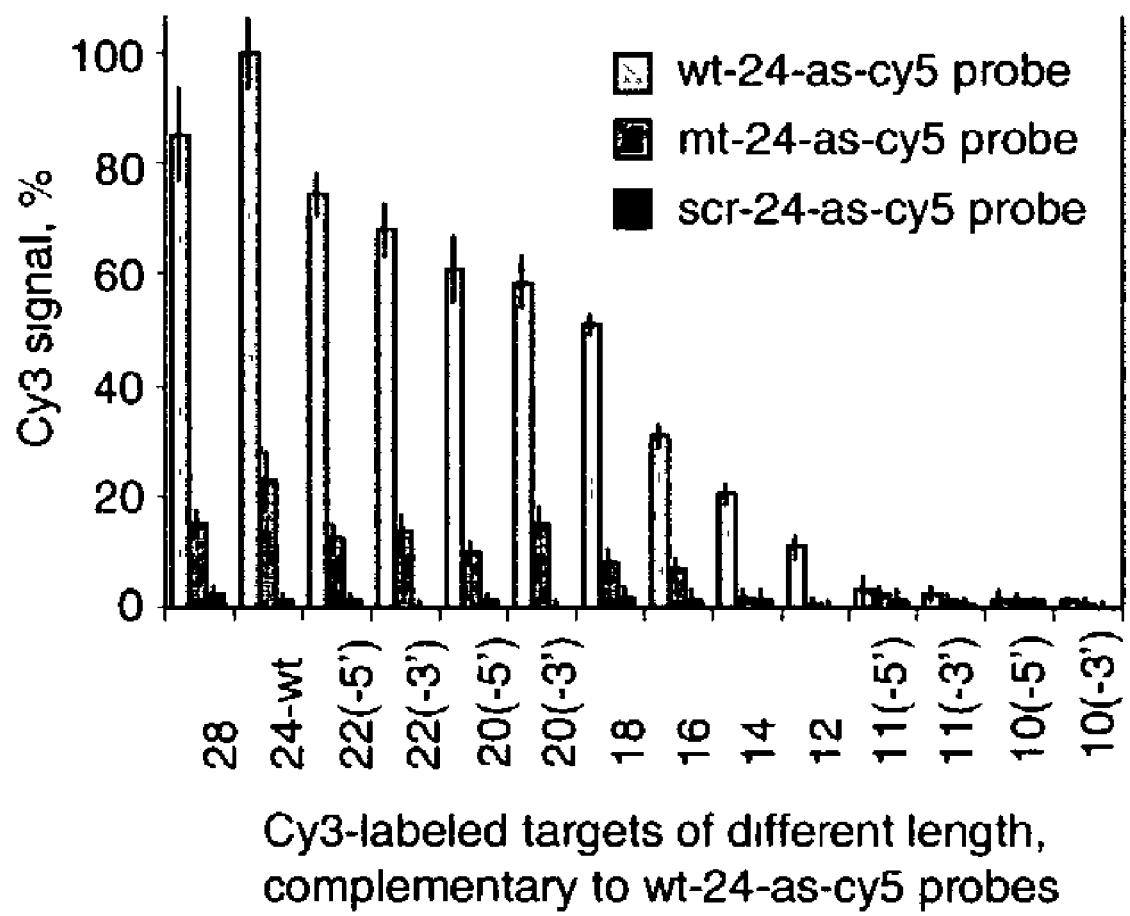
FIG. 7 Length dependence of target hybridization stability upon a 24 base surface-bound probe. The following protocol was employed at room temperature throughout: (1) prehybridization in 60 mM sodium carbonate, 20% formamide, 5× Denhardts, 1.5% polyvinyl alcohol (PVA), pH 9.5 for 1 min, (2) 10 min hybridization at 3 μM of Cy3-labeled targets (10-28 bases) in 60 mM sodium carbonate, 20% formamide, 5× Denhardts, 0.6% PVA, pH=9.5, (3) two rinses in prehybridization buffer, (4) 10 min wash in 60 mM sodium carbonate, 25% formamide, 5× Denhardts, 0.6% PVA, pH=9.5, (5) brief wash in de-ionized $H_2O$, (6) drying. Sequences of oligonucleotides in x axis are provided in Table 1. The arrays used in these experiments are identical to the array shown in FIG. 2A. The bar graphs represent the normalized means and the standard deviations of the mean from 12 array elements.

Although both dissociation kinetics and DNase protection assays have suggested a highly asymmetric duplex structure and are generally inconsistent with a symmetric double helix, such a simple interpretation of the data can only be made if the duplex under study is fully-formed over the span of the surface bound probe. To answer this question, a set of ten Cy3-labeled (green) target oligonucleotides of varied length were synthesized and hybridized to the arrays described in FIG. 2A. Under stringent hybridization and washing conditions, it was found that binding stability to complementary 24-mer probes, printed at 0.3 μM on aminosilanized surface, increased as a function of target length up to the full probe length of 24 bases (FIG. 7) and then leveled thereafter. Throughout, base-pairing specificity was maintained at the level of two base changes per 24-mer probe. This relatively simple outcome suggests that a sequence specific duplex is forming, on average, along the entirety of the available 24 base probe strand, which if the resulting product were a standard B-form helix, would correspond to slightly more than two helical turns.

Example 13

Protocol for Repeatable, Reliable Adsorptive Microarray Formation and Hybridization Preparation of the adsorptive surface. Microscope slides were cleaned in deionizing water, and dried in dust free oven. The adsorptive surface was applied on the surface of the glass by equilibrating adsorptive surface material in a vacuum oven at 82° C., overnight at 27 mm Hg.

Preparation of the oligonucleotide. Presynthesized, linker-free oligonucleotides were dissolved in de-ionized water. Dimethyl sulfoxide (DMSO) was used to uniformly dry the oligonucleotide to create a uniform monolayer on the adsorptive surface. Saturation limits of the surface for the oligonucleotide were calculated by using labeled oligonucleotides and the concentration of the oligonucleotides was maintained over the saturation limits.

Direct adsorption of the oligonucleotides to the surface. Oligonucleotides were adsorbed to the surface by using a robotic machine to dispense controlled, known volumes, such that each drop of the oligonucleotide solution is similar (<1% variation) to the other one on the hybridization device.

Prehybridization. The adsorbed oligonucleotide is incubated with a prehybridization solution containing phosphate buffer (potassium phosphate monobasic, sodium phosphate dibasic, pH 8.0) with 5× Denhardt's solution and 1% sodium dodecyl sulfate (SDS) for 15 minutes.

Hybridization. Hybridization is carried out by applying 20 µL of fluorescently labeled target (full length mRNA, or cDNA) from the sample of interest, and incubated overnight at room temperature under humidifying conditions.

Wash. After a 12 hour hybridization, washing is done in a phosphate buffer with at least up to of half the strength (150 mM) in molarity compared to the binding buffer, without any Denhardt's solution.

Scan. Slides after the wash are dried by centrifugation or heat, are scanned using either a laser or CCD based scanner, to generate a fluorescent image.

Analyze. Fluorescent image intensities are obtained by the quantitation of the spots on the microarray by either applying a grid or by automatic spot finding algorithms.

Example 14

Comparative Example

Figure 8:
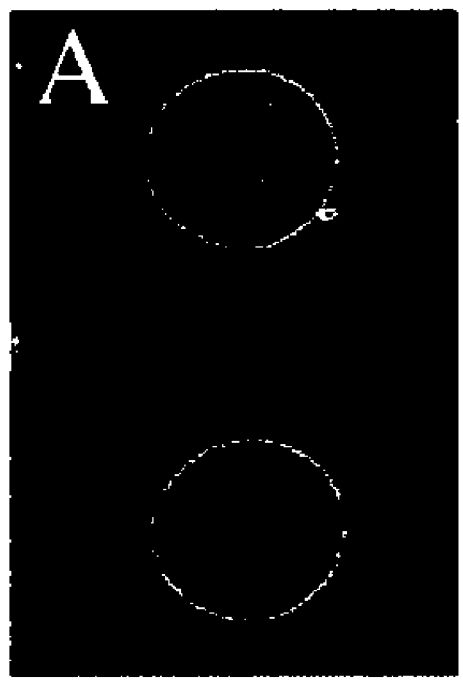
FIG. 8. Stability of adsorbed DNA. Cy3-labeled DNA 50-mer directly adsorbed onto a cationic surface which was formed using vapor deposition (Example 1) was washed for 5 minutes (A) or 24 hours (B). Numerical intensities are shown in Table 2. Cy3-labeled DNA 50-mer directly adsorbed onto a cationic surface which was formed according to the solution-dipped method of CEL Associates (CSA-25; CEL Associates, Inc., Pearland, Tex.) was washed for 5 minutes (C) or 24 hours (D).
Figure 8:
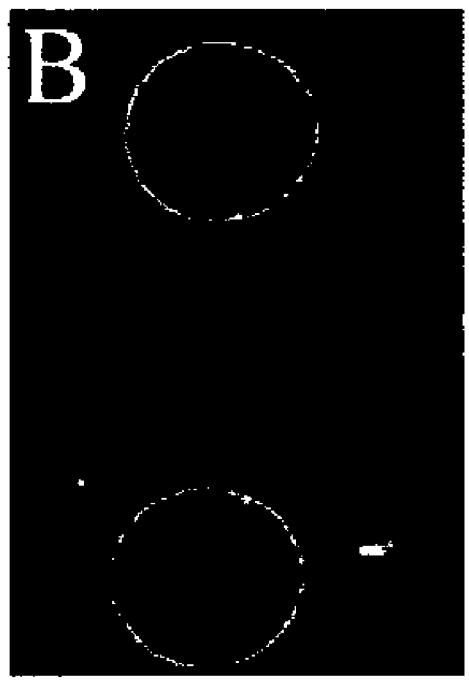
Figure 8:
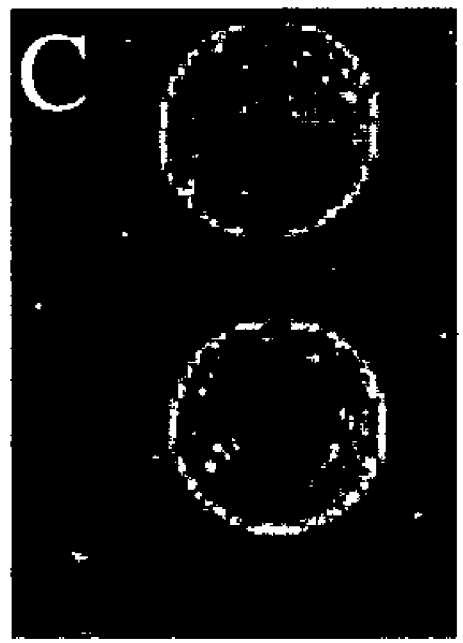
Figure 8:

A first set of Cy3-labeled DNA 50-mers were directly adsorbed onto a uniform cationic surface which was formed using vapor deposition according to Example 1. A second set of Cy3-labeled DNA 50-mers were adsorbed onto a uniform cationic surface which was formed according to the solution dip method of Cel Associates (CSA-25; CEL Associates, Inc., Pearland, Tex.). The surfaces were then washed with the wash buffer of Example 16 for 5 minutes or 24 hours. The fluorescent intensity of the DNA remaining after washing is shown in FIG. 8 and Table 2. Fluorescent intensity after five minutes of washing is substantially the same as at time zero. However, background at time zero was undetectable.

TABLE 2

Cy3-labeled oligodeoxyribonucleotides directly adhered to a surface.

| FIG. 8 | Example 1 | | Cel Associates | |
|---|---|---|---|---|
| | A | B | C | D |
| Wash | 5 min | 24 h | 5 min | 24 h |
| Spot Intensity | 1208 | 1139 | 1023 | 192 |
| Background | 26 | 21 | 369 | 79 |
| Signal/Background | 46.5 | 54 | 2.8 | 2.4 |

Example 15

Effect of Capping on Hybridization

A 40-mer DNA probe printed at 1.0 µM was hybridized with a perfectly matched target 40-mer. The target 40-mer was hybridized at total concentration of 1.0 µM comprising 0.1 µM Cy3-labeled target. Two methods of capping were used. Chemical capping was achieved by a vapor phase method wherein 0.5 M acetic anhydride in DMF at 50° C. and 25 inches of mercury for 16 hours followed by a liquid phase of 0.5 M succinic anhydride in DMF at room temperature for 1 h. Alternatively, surfactant capping was achieved by using SDS in the prehybridization buffer.

Figure 9A:
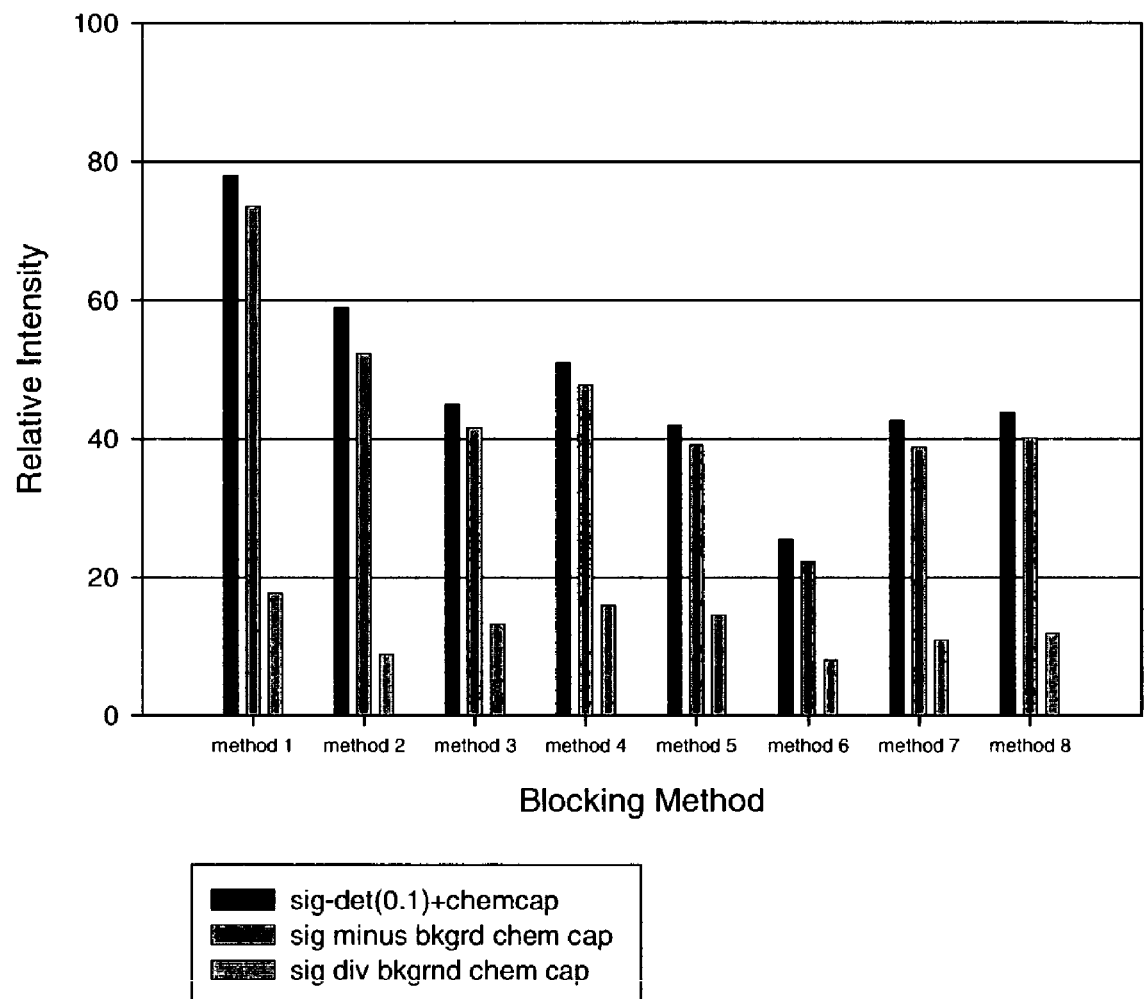
FIG. 9. Effect of capping and hybridization conditions on detection of probe-target duplex formation. Absolute signal, absolute signal minus background fluorescence, and the ratio of signal to background is shown for capped (A) and uncapped (B) DNA microarrays printed with 40-mer probes.
Figure 9B:
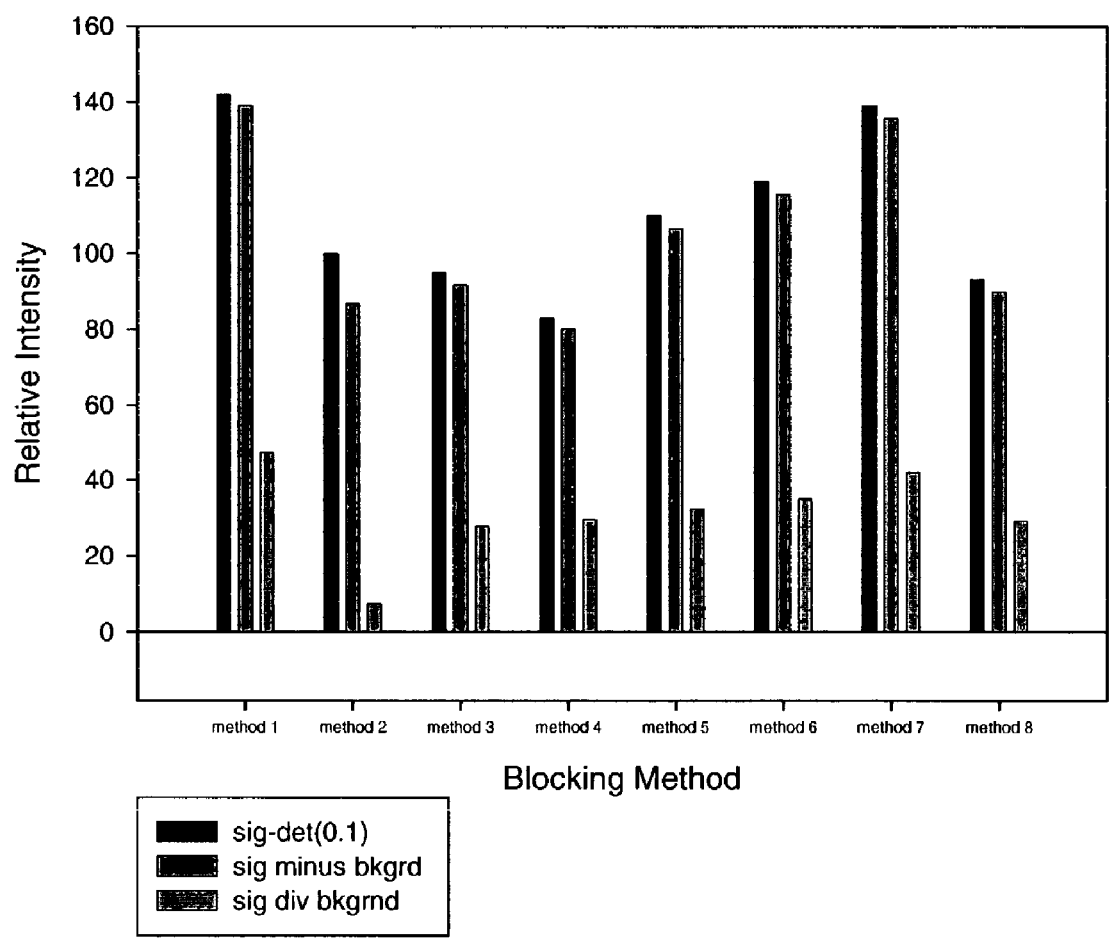

Approximately 40 prehybridization/hybridization buffer combinations were tested for blocking efficiency. All displayed satisfactory performance. Eight of the preferred combinations appear in Table 3 and FIG. 9.

TABLE 3

Prehybridization and Hybridization Buffer Compositions.

| | Prehybe | Hybe |
|---|---|---|
| Method 1 | 1% SDS<br>5X Denhardt's<br>300 mM pH 8.0 Buffer | 1% SDS<br>5X Denhardt's<br>300 mM pH 8.0 Buffer |
| Method 2 | 1% SDS<br>300 mM pH 8.0 Buffer | 0.2 µg/µl cot1 dna<br>1.0% BSA<br>300 mM pH 8.0 Buffer |
| Method 3 | 1% SDS<br>5X Denhardt's<br>300 mM pH 9.5 Buffer | 1% SDS<br>5X Denhardt's<br>300 mM pH 9.5 Buffer |
| Method 4 | 1% SDS<br>5X Denhardt's<br>300 mM pH 9.5 Buffer | 0.2 µg/µl cot1 dna<br>5X Denhardt's<br>300 mM pH 9.5 Buffer |
| Method 5 | 1% SDS<br>5X Denhardt's<br>300 mM pH 0.5 Buffer | 5X Denhardt's<br>300 mM pH 9.5 Buffer |
| Method 6 | 1% SDS<br>5X Denhardt's<br>300 mM pH 9.5 Buffer | 300 mM pH 9.5 Buffer |
| Method 7 | 1% SDS<br>5X Denhardt's<br>300 mM pH 8.0 Buffer | 1% SDS<br>0.2 µg/µl cot1 dna<br>5X Denhardt's<br>300 mM pH 8.0 Buffer |
| Method 8 | 1% SDS<br>5X Denhardt's<br>300 mM pH 8.0 Buffer | 0.2 µg/µl cot1 dna<br>5X Denhardt's<br>300 mM pH 8.0 Buffer |

Unlike conventional chemical capping used in the literature, a surfactant like SDS effectively blocks non-specific binding. The conventional capping method results in an average intensity of hybridization of 77 fluorescent units and using the surfactant method almost doubles the intensity of the signal of hybridization to 150 fluorescent units.

Example 16

Adsorptive Microarrays may be Used to Detect Solution-State cDNA

Probes were 60-mers of predetermined sequence (derived from mouse p53-related genes) and were adsorbed onto a glass surface according to Example 13.

Figure 10:
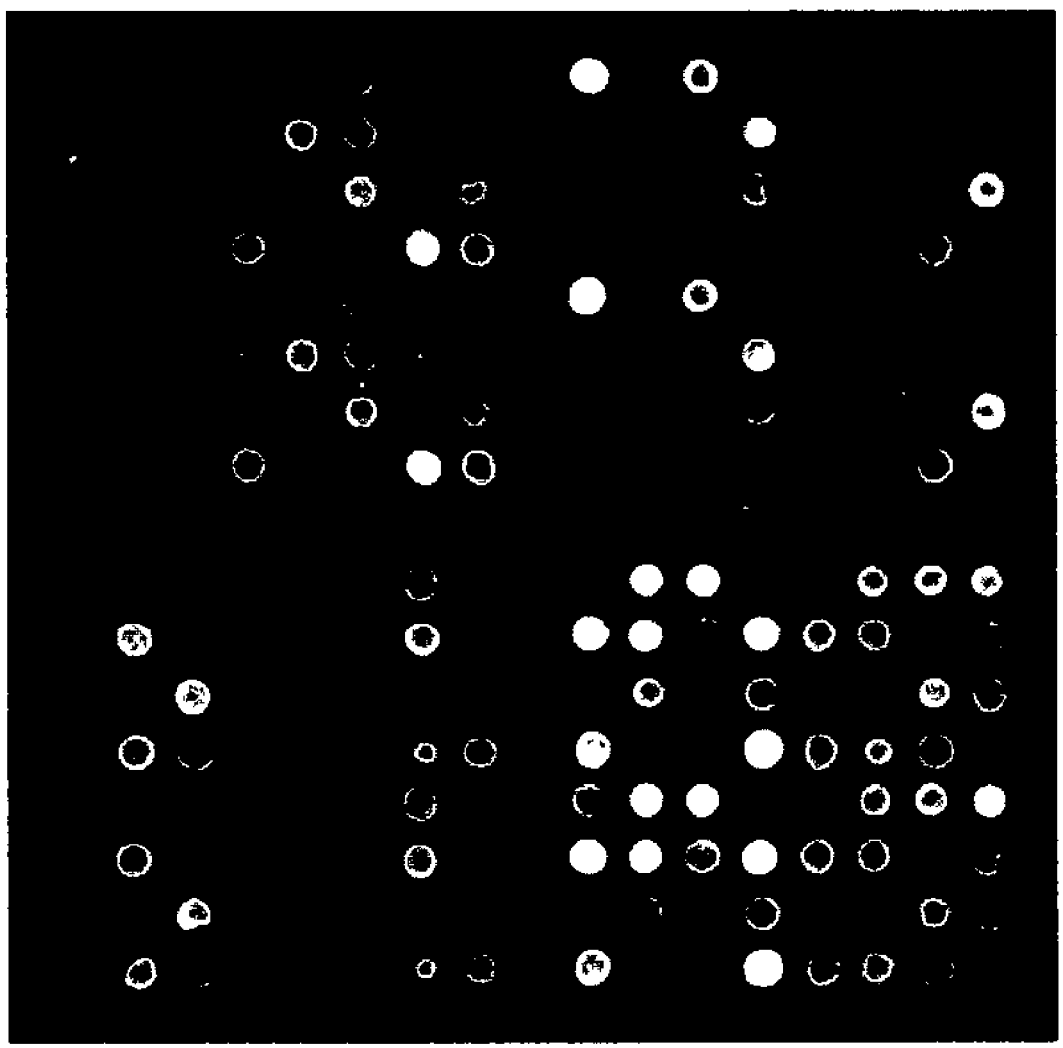
FIG. 10. Adsorptive microarray hybridized with cDNA targets derived from untreated (green) or γ-irradiated (red) mouse thymus tissue.

Targets for hybridization to the microarray were prepared as follows—Total cellular RNA was extracted from untreated and γ-irradiated mouse thymus tissues, by a modified guanidine-isothiocyanate technique (Qiagen, Valencia, Calif., USA). The quality and the concentration of the RNA were checked using both spectrometric and dye tests (Invitrogen, Carlsbad, Calif., USA). 10 µg of total cellular RNA from untreated mouse thymus tissue was reverse transcribed using MMLV-RT (Clontech, Palo Alto, Calif., USA) in presence of Cy3 dye (Amersham Biosciences, Piscataway, N.J.) which resulted in Cy3 labeled mRNA from untreated mouse thymus. 10 µg of total cellular RNA from γ-irradiated mouse thymus tissue was reverse transcribed using MMLV-RT (Clontech, Palo Alto, Calif., USA) in presence of Cy5 dye (Amersham Biosciences, Piscataway, N.J.) which resulted in Cy5 labeled mRNA from untreated mouse thymus, using reverse transcription protocols supplied by Clontech in the MMLV-RT kit. The resulting labeled cDNA was precipitated by incubation in 95% ethanol for 1 hour at −70° C., and the precipitate was pelleted using a microcentrifuge at 12,000 rpm for 10 minutes. The pellet was washed in 70% ethanol and air dried. The dried pellet was dissolved in the hybridization buffer. Equal amounts of Cy3 and Cy5 labeled cDNA targets were added to the microarray and incubated at room temperature in a humidifying chamber for 12 hours. After 12 hours, the unbound target was removed by washing the microarray with washing buffer on an orbital shaker for 30 minutes with buffer changes every 10 minutes. At the end of 30 minutes, the microarray was air dried and scanned in a CCD imager (Array Worx, Applied Precision, Inc. Issaquah, Wash., USA). The resulting image is read as follows, for each spot on the array, the amount of green intensity signifies the level of untreated gene and the amount of red intensity signifies the level of γ-irradiated gene. Yellow color signifies equal levels of gene expression from both the samples (FIG. 10).

Pre-hybridization buffer and hybridization buffer comprised 300 mM phosphate buffer (0.017 M monobasic sodium phosphate, (monohydrate)), 0.305 M dibasic sodium phosphate, pH 8.0; 5× Denhardt's solution (0.1% Ficoll (type 400), 0.1% polyvinylpyrrolidone, and 0.1% bovine serum albumin); and 1% Sodium Dodecyl Sulfate.

Washing buffer was 150 mM phosphate buffer (0.0085 M monobasic sodium phosphate, (monohydrate), 0.15 M dibasic sodium phosphate, pH 8.0); 1% Sodium Dodecyl Sulfate.

REFERENCES

The documents cited throughout this application are incorporated herein in their entirety by reference. Citation of these documents should not be construed as an admission that such documents constitute prior art against the instant invention.

---

We claim:

1. A biomolecular hybridization device comprising:
   a substrate having an aminosilanized surface permanently and covalently attached thereto; and
   an adsorbed monolayer formed from an about twice saturating amount of unmodified single-stranded oligonucleotides all of which are about 12 to 16 bases in length adsorbed to the aminosilanized surface as a saturated film of constrained oligonucleotides on the surface via direct non-covalent phosphate-surface adsorptive contact of substantially all phosphate groups of each oligonucleotide at a density of one phosphate group per about 1.5 square nanometers of surface, wherein each constrained oligonucleotide base plane is presented from the surface in a manner effective to dissociably hybridize to a complementary single-stranded nucleic acid with asymmetric, substantially non-helical base pairing without alteration of the oligonucleotide base plane presentation and without oligonucleotide phosphate group dissociation from the surface.

2. The biomolecular hybridization device of claim 1 wherein said device further comprises a single-stranded nucleic acid reversibly hybridized to the oligonucleotides as a substantially non-helical duplex of 12 to 16 base pairs long adsorbed to said, surface.

3. The biomolecular hybridization device of claim 1 wherein the form of said substrate is a slide or a bead.

4. The biomolecular hybridization device of claim 2 wherein the nucleic acid is DNA.

5. The biomolecular hybridization device of claim 2 wherein the nucleic acid is RNA.

6. The biomolecular hybridization device of claim 1 further comprising a capping material disposed on said surface.

7. The method biomolecular hybridization device of claim 6 wherein said capping material is comprises deposition of a surfactant or an acid anhydride.

* * * * *

SEQUENCE LISTING

<160> NUMBER OF SEQ ID NOS: 24

<210> SEQ ID NO 1
<211> LENGTH: 12
<212> TYPE: DNA
<213> ORGANISM: Artificial Sequence
<220> FEATURE:
<223> OTHER INFORMATION: Oligonucleotide wt-12-as

<400> SEQUENCE: 1
ctgtagtggg cg                                                      12

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide mt-12-as

<400> SEQUENCE: 2
ctgtagaggg cg                                                      12

<210> SEQ ID NO 3
<211> LENGTH: 12
<212> TYPE: DNA
<213> ORGANISM: Artificial Sequence
<220> FEATURE:
<223> OTHER INFORMATION: Oligonucleotide scr-12-as

<400> SEQUENCE: 3
gtcgtggagc gt                                                      12

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide wt-24-a

<400> SEQUENCE: 4
ctgtagtggg cgtcctgctg ttcc                                          24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide mt-24-as

<400> SEQUENCE: 5
ctgtagaggg cgtccagctg ttcc                                          24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide scr-24-as

<400> SEQUENCE: 6
tggtgcggtg acaagctcct cctg                                          24

<210> SEQ ID NO 7
<211> LENGTH: 12
<212> TYPE: DNA
<213> ORGANISM: Artificial Sequence
<220> FEATURE:
<223> OTHER INFORMATION: Oligonucleotide wt-12-s

<400> SEQUENCE: 7
cgcccactac ag                                                       12

<210> SEQ ID NO 8
<211> LENGTH: 12
<212> TYPE: DNA
<213> ORGANISM: Artificial Sequence
<220> FEATURE:
<223> OTHER INFORMATION: Oligonucleotide mt-12-s

<400> SEQUENCE: 8
cgccctctac ag                                                       12

<210> SEQ ID NO 9
<211> LENGTH: 12
<212> TYPE: DNA
<213> ORGANISM: Artificial Sequence
<220> FEATURE:
<223> OTHER INFORMATION: Oligonucleotide scr-12-s

<400> SEQUENCE: 9
acgctccacg ac                                                       12

<210> SEQ ID NO 10
<211> LENGTH: 24
<212> TYPE: DNA
<213> ORGANISM: Artificial Sequence
<220> FEATURE:

```
<223> OTHER INFORMATION: Oligonucleotide wt-24-s

<400> SEQUENCE: 10
ggaacagcag gacgcccact acag                                          24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide mt-24-s

<400> SEQUENCE: 11
ggaacagctg gacgccctct acag                                          24

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide scr-24-s

<400> SEQUENCE: 12
caggaggagc ttgtcaccgc acca                                          24

<210> SEQ ID NO 13
<211> LENGTH: 10
<212> TYPE: DNA
<213> ORGANISM: Artificial Sequence
<220> FEATURE:
<223> OTHER INFORMATION: Oligonucleotide wt-10-s-(-3')

<400> SEQUENCE: 13
cgcccactac                                                          10

<210> SEQ ID NO 14
<211> LENGTH: 10
<212> TYPE: DNA
<213> ORGANISM: Artificial Sequence
<220> FEATURE:
<223> OTHER INFORMATION: Oligonucleotide wt-10-s-(-5')

<400> SEQUENCE: 14
cccactacag                                                          10

<210> SEQ ID NO 15
<211> LENGTH: 11
<212> TYPE: DNA
<213> ORGANISM: Artificial Sequence
<220> FEATURE:
<223> OTHER INFORMATION: Oligonucleotide wt-11-s-(-3')

<400> SEQUENCE: 15
cgcccactac a                                                        11

<210> SEQ ID NO 16
<211> LENGTH: 11
<212> TYPE: DNA
<213> ORGANISM: Artificial Sequence
<220> FEATURE:
<223> OTHER INFORMATION: Oligonucleotide wt-11-s-(-5')

<400> SEQUENCE: 16
gcccactaca g                                                        11
```

```
<210> SEQ ID NO 17
<211> LENGTH: 14
<212> TYPE: DNA
<213> ORGANISM: Artificial Sequence
<220> FEATURE:
<223> OTHER INFORMATION: Oligonucleotide wt-14-s

<400> SEQUENCE: 17
gacgcccact acag                                                         14

<210> SEQ ID NO 18
<211> LENGTH: 16
<212> TYPE: DNA
<213> ORGANISM: Artificial Sequence
<220> FEATURE:
<223> OTHER INFORMATION: Oligonucleotide wt-16-s

<400> SEQUENCE: 18
aggacgccca ctacag                                                       16

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide wt-18-s

<400> SEQUENCE: 19
gcaggacgcc cactacag                                                     18

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide wt-20-s-(-3')

<400> SEQUENCE: 20
aacagcagga cgcccactac                                                   20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide wt-20-s-(-5')

<400> SEQUENCE: 21
cagcaggacg cccactacag                                                   20

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide wt-22-s-(-3')

<400> SEQUENCE: 22
ggaacagcag gacgcccact ac                                                22

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide wt-22-s-(-5')
```

```
<400> SEQUENCE: 23
aacagcagga cgcccactac ag                                               22

<210> SEQ ID NO 24
<211> LENGTH: 28
<212> TYPE: DNA
<213> ORGANISM: Artificial Sequence
<220> FEATURE:
<223> OTHER INFORMATION: Oligonucleotide wt-28-s

<400> SEQUENCE: 24
caggaacagc aggacgccca ctacagtt                                         28
```